United States Patent
Cronenberg et al.

(10) Patent No.: US 9,950,119 B2
(45) Date of Patent: Apr. 24, 2018

(54) DRUG RECONSTITUTION SYSTEM

(71) Applicant: Becton, Dickinson and Company, Franklin Lakes, NJ (US)

(72) Inventors: Richard Cronenberg, Mahwah, NJ (US); Haiming Wu, North Attleboro, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 477 days.

(21) Appl. No.: 14/377,585

(22) PCT Filed: Mar. 8, 2013

(86) PCT No.: PCT/US2013/029807
§ 371 (c)(1),
(2) Date: Aug. 8, 2014

(87) PCT Pub. No.: WO2013/134614
PCT Pub. Date: Sep. 12, 2013

(65) Prior Publication Data
US 2016/0015900 A1  Jan. 21, 2016

Related U.S. Application Data

(60) Provisional application No. 61/608,451, filed on Mar. 8, 2012.

(51) Int. Cl.
*A61M 5/315* (2006.01)
*A61M 5/19* (2006.01)
(Continued)

(52) U.S. Cl.
CPC ........ *A61M 5/31505* (2013.01); *A61J 1/2048* (2015.05); *A61M 5/19* (2013.01);
(Continued)

(58) Field of Classification Search
CPC .......... A61J 1/20; A61J 1/2003; A61J 1/2051; A61J 1/2055; A61J 1/2065; A61J 1/2089;
(Continued)

(56) References Cited

U.S. PATENT DOCUMENTS 3,835,835 A    9/1974  Thompson et al.
4,543,093 A *  9/1985  Christinger ....... A61M 5/31513
                                                    604/228
(Continued)

FOREIGN PATENT DOCUMENTS

EP           1541185 A1     6/2005

*Primary Examiner* — Bhisma Mehta
*Assistant Examiner* — James D Ponton
(74) *Attorney, Agent, or Firm* — The Webb Law Firm

(57) ABSTRACT

A system including an adapter (14) for sequential engagement with a cartridge (18) containing a first substance and a vial (16) containing a second substance is disclosed. The adapter is configured to first engage with the vial and subsequently engage with the cartridge such that the cartridge is in fluid communication with the vial via the adapter. The system includes a latch member (150) engageable with a portion of the cartridge. A plunger rod (44) includes a protrusion (50) and is adapted to communicate with the latch member, the plunger rod being transitionable from a disengaged position, in which the protrusion of the plunger rod is disengaged from the latch member and the latch member is locked to the cartridge, to an engaged position, in which the protrusion is engaged with the latch member and the latch member is unlocked from the cartridge and locked to the plunger rod.

14 Claims, 21 Drawing Sheets

(51) Int. Cl.
*A61M 5/24* (2006.01)
*A61J 1/20* (2006.01)

(52) U.S. Cl.
CPC ............ *A61M 5/24* (2013.01); *A61M 5/2448* (2013.01); *A61M 5/31596* (2013.01); *A61M 2005/31508* (2013.01); *A61M 2202/064* (2013.01)

(58) Field of Classification Search
CPC .... A61J 1/2096; A61J 1/2048; A61M 5/2066; A61M 5/2448; A61M 5/284; A61M 5/31596; A61M 2005/2451; A61M 5/31505
See application file for complete search history.

(56) References Cited

U.S. PATENT DOCUMENTS

| | | | |
|---|---|---|---|
| 6,123,688 A * | 9/2000 | Botich | A61M 5/24 604/110 |
| 2004/0024354 A1* | 2/2004 | Reynolds | A61F 13/0203 604/87 |
| 2005/0137566 A1* | 6/2005 | Fowles | A61J 1/1406 604/412 |
| 2007/0016143 A1 | 1/2007 | Miller et al. | |
| 2007/0179452 A1* | 8/2007 | Kosinski | A61M 5/31511 604/218 |
| 2011/0106045 A1* | 5/2011 | Reynolds | A61J 1/2096 604/413 |

* cited by examiner

DRUG RECONSTITUTION SYSTEM

BACKGROUND OF THE INVENTION

1. Field of the Disclosure

The present disclosure relates generally to drug reconstitution systems. More particularly, the present disclosure relates to a drug reconstitution system that reduces opportunities for user error.

2. Description of the Related Art

Certain drugs are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection.

In addition, drugs may be provided as multipart systems which require mixing prior to administration. For example, one or more liquid components, such as flowable slurries, and one or more dry components, such as powdered or granular components, may be provided in separate containers which require mixing prior to administration.

There are a number of devices and methods for drug reconstitution. The most common method is to inject a diluent contained in a syringe into a vial containing a dry component of the drug. After shaking the vial to mix the dry and liquid components, the user withdraws the reconstituted drug fluid from the vial using a second syringe. The second syringe is then used to inject the reconstituted drug to a patient. This reconstitution process is labor intensive and introduces numerous opportunities for contamination of the needle tip or vial contents. In addition, there is also a danger that the patient or practitioner will accidently be pricked by the exposed needle. These steps are even more intimidating for a patient attempting to self-inject a reconstituted drug for the first time. Further, the needle of the injection syringe may be dulled by insertion through the vial stopper. A dulled needle is more likely to be painful and/or cause scarring when later inserted into a patient.

Numerous prior art devices seek to simplify the process of reconstituting a drug and injecting the reconstituted drug into a patient. For example, a common transfer assembly includes a syringe with a removable cartridge. The liquid component of the drug is forced from the cartridge to a vial for reconstitution with a dry component of the drug. The reconstituted fluid is then drawn back into the cartridge. The cartridge can then be removed from the transfer assembly and inserted into an injection syringe to deliver the fluid to the patient. This type of transfer device is generally larger and more complex than a typical syringe. Specifically, the device must include a structure to allow a user to easily remove the filled cartridge. In addition, the injection syringe must be compatible with the transfer device so that the cartridge removed from the transfer device can be inserted into the injection syringe.

Alternatively, an injector may be configured to permit mixing of dry and wet drug components prior to injection. To achieve mixing of substances in pen injectors, prior art devices have been developed that provide the wet component (e.g., liquid) and the dry component (e.g., powder) in separate chambers of a common container. The container is configured to permit the flow of the wet component to the dry component through a bypass channel to cause mixing thereof in preparing a solution for injection. However, these devices suffer several drawbacks. For example, these containers must be specifically configured for mixing and, typically, are more expensive to manufacture than conventional containers. In addition, these containers typically have a substantial amount of wasted dead space (e.g., volume of wasted dead space may be four to five times the volume of the accommodated substance). The excess wasted dead space results in larger-size containers, which may be less convenient to handle and more inaccurate for dosing purposes.

In view of the deficiencies of current methods and devices for drug reconstitution and injection, there is a need for a simpler device for reconstituting a drug and transferring the reconstituted drug to an injector for injection to a patient. Further, the system should reduce opportunities for user error by preventing exposure of needles before, during, and after use. Similarly, the system should reduce the opportunity for contamination by reducing the number of times that a needle must be inserted and removed from a drug vial or cartridge.

SUMMARY OF THE INVENTION

The present disclosure provides a system which, in one embodiment, includes an adapter for sequential engagement with a cartridge containing a first substance and a vial containing a second substance. The adapter is configured to first engage with the vial and with the vial engaged with the adapter, the adapter is configured to engage with the cartridge such that after an activation step the cartridge is in fluid communication with the vial via the adapter. In this manner, the system prevents unintentional loss of the first substance from the cartridge. The system further includes a latch member engageable with a portion of a cartridge and a portion of a plunger rod. The plunger rod includes a protrusion and is adapted to communicate with the latch member. The plunger rod is transitionable from a disengaged position, in which the protrusion of the plunger rod is disengaged from the latch member and the latch member is locked to the cartridge, to an engaged position, in which the protrusion is engaged with the latch member and the latch member is unlocked from the cartridge and locked to the plunger rod. With the latch member locked to the cartridge, only actuation of the plunger rod protrusion can unlock the latch member from the cartridge.

A locking member may be connected to the cartridge to prevent a stopper from sliding out of the cartridge. In this manner, the locking member prevents accidental removal of the stopper from the cartridge and prevents a plunger rod from further actuating the stopper to expel a substance contained in the cartridge. In certain configurations, with the latch member locked to the plunger rod, one-handed swirling is enabled to mix substances contained in a vial provided in fluid communication with the cartridge via the adapter of the present disclosure.

In accordance with another embodiment of the present invention, a system includes a cartridge having a cartridge distal end, a cartridge proximal end, and a sidewall extending therebetween and defining a chamber having an interior. The system further includes a stopper slidably disposed within the interior of the cartridge. The system further includes a latch member engageable with a portion of the cartridge and a portion of the plunger rod and a plunger rod engageable with a portion of the stopper and adapted to communicate with the latch member. The plunger rod includes a protrusion, and the plunger rod is transitionable from a disengaged position, in which the protrusion of the plunger rod is disengaged from the latch member and the latch member is locked to the cartridge, to an engaged position, in which the protrusion is engaged with the latch member and the latch member is unlocked from the cartridge and locked to the plunger rod.

In one configuration, the plunger rod further includes a plunger rod distal end engageable with the portion of the stopper and a plunger rod proximal end, the protrusion extending from the plunger rod adjacent the plunger rod proximal end. In another configuration, with the plunger rod in the disengaged position, the latch member is locked to the cartridge proximal end. In one configuration, the stopper is slidably disposed within the interior of the cartridge between a first position adjacent the cartridge proximal end and a second position adjacent the cartridge distal end.

In one configuration, with the stopper in the first position the plunger rod is in the disengaged position. In another configuration, with the stopper in the second position the plunger rod is in the engaged position. In one configuration, a portion of the plunger rod is sized for movement within the cartridge interior from the disengaged position to the engaged position. In one configuration, a portion of the plunger rod is sized for movement within the interior of the cartridge from the disengaged position to the engaged position. In one configuration, the system further includes a first substance contained within the chamber of the cartridge.

In accordance with another embodiment of the present invention, a system includes a cartridge having a cartridge distal end, a cartridge proximal end, and a sidewall extending therebetween and defining a cartridge chamber, a first substance contained within the cartridge chamber, and a stopper slidably disposed within the cartridge chamber. A latch member is engageable with a portion of the cartridge and a portion of the plunger rod, and a plunger rod is engageable with a portion of the stopper and adapted to communicate with the latch member. The plunger rod includes a protrusion, and the plunger rod is transitionable from a disengaged position, in which the protrusion of the plunger rod is disengaged from the latch member and the latch member is locked to the cartridge, to an engaged position, in which the protrusion is engaged with the latch member and the latch member is unlocked from the cartridge and locked to the plunger rod. The system further includes a vial defining a vial chamber, a second substance contained within the vial chamber, and an adapter having a first end adapted to engage the vial and a second end adapted to engage the cartridge after engagement with the vial.

In accordance with a further embodiment of the present invention, a system includes a cartridge having a cartridge distal end, a cartridge proximal end, and a sidewall extending therebetween and defining a cartridge chamber and a first substance contained within the cartridge chamber. The system of this embodiment includes a vial defining a vial chamber and a second substance contained within the vial chamber. The system further includes an adapter adapted for sequential engagement with the vial and the cartridge.

In one configuration, the adapter is adapted to first engage with the vial. In one configuration, with the vial engaged with the adapter, the adapter is adapted to engage with the cartridge such that the cartridge chamber is in fluid communication with the vial chamber via the adapter. In one configuration, the system further includes an actuation member adapted to expel the first substance from the cartridge chamber to the vial chamber via the adapter. In one configuration, the actuation member includes a stopper slidably disposed within the cartridge chamber between a first position adjacent the cartridge proximal end and a second position adjacent the cartridge distal end, and a plunger rod that includes a plunger rod distal end engageable with a portion of the stopper, a plunger rod proximal end, and a portion of the plunger rod sized for movement within the cartridge chamber to actuate the stopper between the first position and the second position. In one configuration, actuation of the stopper from the first position to the second position by the plunger rod expels the first substance from the cartridge chamber to the vial chamber via the adapter. In one configuration, the first substance includes a diluent. In one configuration, the second substance includes a powder.

In accordance with another embodiment of the present invention, a system includes a cartridge having a cartridge distal end, a cartridge proximal end, and a sidewall extending therebetween and defining a chamber having an interior. The system of this embodiment includes a stopper slidably disposed within the interior of the cartridge between a first position adjacent the cartridge proximal end and a second position adjacent the cartridge distal end. The system further includes a locking member connected to the cartridge and adapted to prevent the stopper from sliding out of the cartridge.

In one configuration, the stopper defines a stopper outer diameter and the locking member defines a locking member inner diameter, the locking member inner diameter being less than the stopper outer diameter, thereby the locking member provides a physical barrier preventing the stopper from sliding out of the cartridge. In another configuration, the locking member is connected adjacent to the cartridge proximal end. In one configuration, the system further includes a plunger rod having a plunger rod distal end engageable with a portion of the stopper, a plunger rod proximal end, and a deformable restraining member transitionable between a deformed position to an undeformed position, a portion of the plunger rod sized for movement within the interior of the cartridge to actuate the stopper between the first position and the second position. In one configuration, with the plunger rod in an initial position the locking member deforms the restraining member of the plunger rod so that the plunger rod is capable of actuating the stopper from the first position to the second position. In one configuration, after the plunger rod actuates the stopper from the first position to the second position, as the plunger rod returns the stopper from the second position back to the first position and the restraining member of the plunger rod is advanced beyond the locking member, the restraining member of the plunger rod moves to its undeformed position and locks to the locking member, thereby the locking member prevents the plunger rod from actuating the stopper again from the first position to the second position.

In accordance with another embodiment of the present invention, a system includes a cartridge having a cartridge distal end, a cartridge proximal end, and a sidewall extending therebetween and defining a cartridge chamber. The system of this embodiment includes a first substance contained within the cartridge chamber, a vial defining a vial chamber, a second substance contained within the vial chamber, and an adapter adapted for sequential engagement with the vial and the cartridge, the adapter having an adapter connection portion securable to the cartridge distal end. The system further includes an injector assembly for injecting a substance, the injector assembly having an injector connection portion, wherein the cartridge distal end is not connectable to the injector connection portion and the adapter connection portion is connectable to the injector connection portion.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
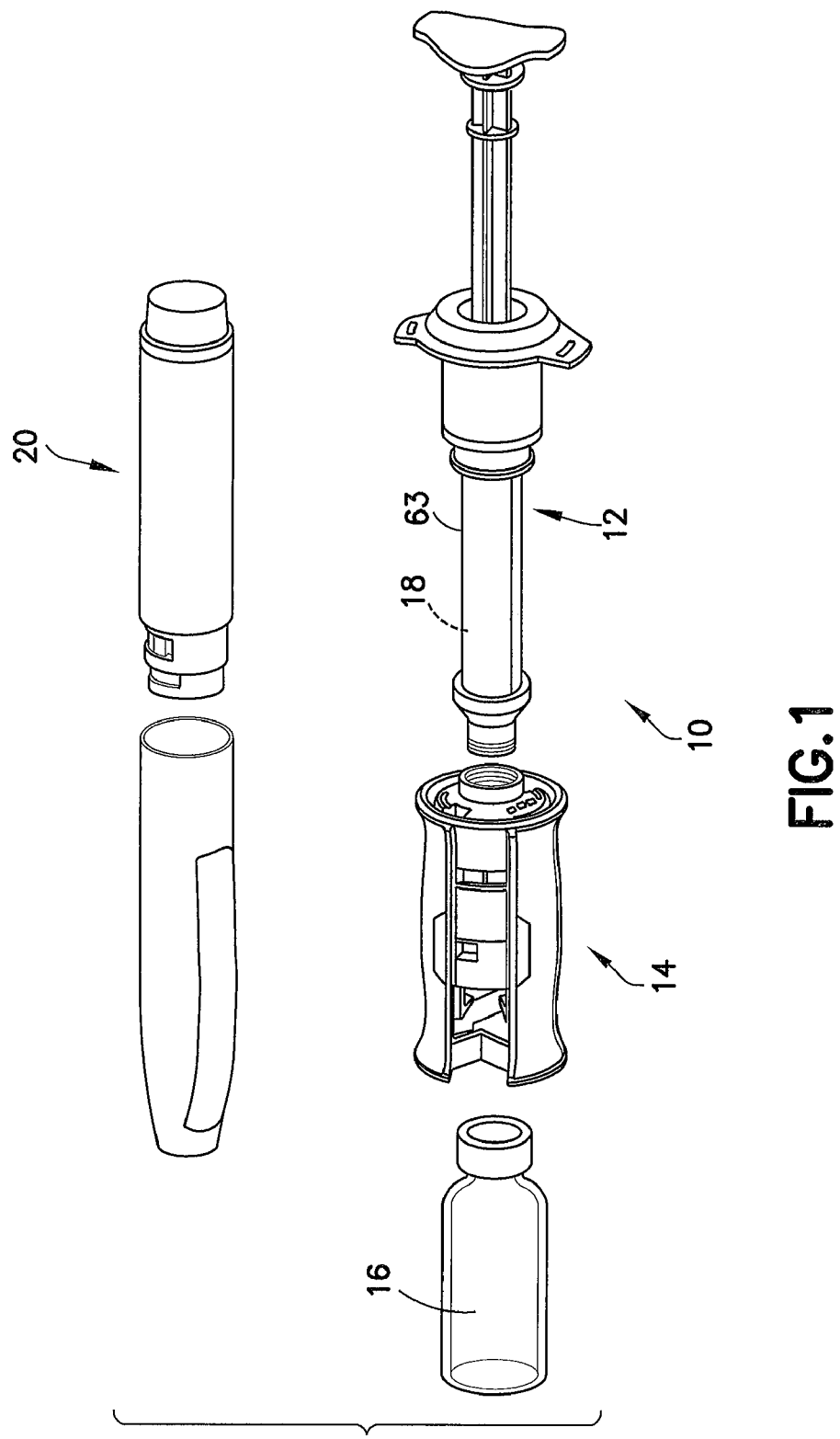
FIG. 1 is an exploded perspective view of a drug reconstitution system in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a syringe assembly adapted for contact with a patient and/or engagement with a separate device such as a needle assembly or IV connection assembly, and "proximal" refers to the opposite direction of distal, i.e., away from the end of a syringe assembly adapted for engagement with the separate device. For purposes of this disclosure, the above-mentioned references are used in the description of the components of a syringe assembly in accordance with the present disclosure.

Referring to FIGS. 1-6, drug reconstitution system 10 includes cartridge housing 12, adapter assembly 14, drug vial 16, and cartridge 18 each sequentially engageable with opposite ends of the adapter assembly 14 as will be described in more detail below. Drug reconstitution system 10 is also adaptable to be used with an injector, such as pen injector 20, as shown in FIG. 1, to allow a user to perform a standard injection as will be described in more detail below.

In one embodiment, cartridge 18 contains a first substance or flowable substance (e.g., slurry or liquid) such as a diluent, and vial 16 contains a second substance, such as a powdered or granular substance intended for reconstitution.

Referring to FIGS. 1-5, cartridge 18 includes barrel 30 defined by barrel sidewall 36 extending between cartridge distal or forward end 32 and proximal or rearward end 34, thereby defining cartridge or interior chamber 38 of cartridge 18. Barrel 30 may be in the general form of an elongated cylindrical barrel as is known in the art for the general shape of a hypodermic syringe, although other forms for containing a fluid for delivery are also contemplated by the present invention. Additionally, barrel 30 may be formed of glass, or may be injection molded from thermoplastic material such as polypropylene, polyethylene, and/or cyclic olefin, according to techniques known to those of ordinary skill in the art, though it is to be appreciated that barrel 30 may be made from other suitable materials and according to other applicable techniques.

In one embodiment, barrel 30 may include markings, such as graduations on sidewall 36 thereof, for providing an indication as to the level or amount of fluid contained within barrel 30. Such markings may be provided on the external wall, the internal wall, or integrally formed or otherwise within the wall of barrel 30. Alternatively, or in addition thereto, the markings may provide a description of the contents of the barrel, or other identifying information, as may be known in the art.

Interior chamber 38 of cartridge 18 may be adapted to contain a flowable material, such as a liquid diluent or other substance intended for drug reconstitution therein. The flowable material may be a liquid or slurry component of a drug or medicament. It is further understood that the flowable material may include one or more constituent elements (e.g., two different types of drug components) containing one or more pharmacologically active agents. Alternatively, the flowable material may serve solely as a diluent for a dry drug and contain no pharmacologically active elements.

In one embodiment, interior chamber 38 of cartridge 18 may be pre-filled with the liquid diluent or other substance intended for drug reconstitution. In this manner, cartridge 18 and/or cartridge housing 12 can be manufactured, pre-filled with a diluent, sterilized, and packaged in appropriate packaging for delivery, storage, and use by the end user. Distal end 32 of cartridge 18 terminates in a tip 37 having an outlet opening 39.

Figure 4:
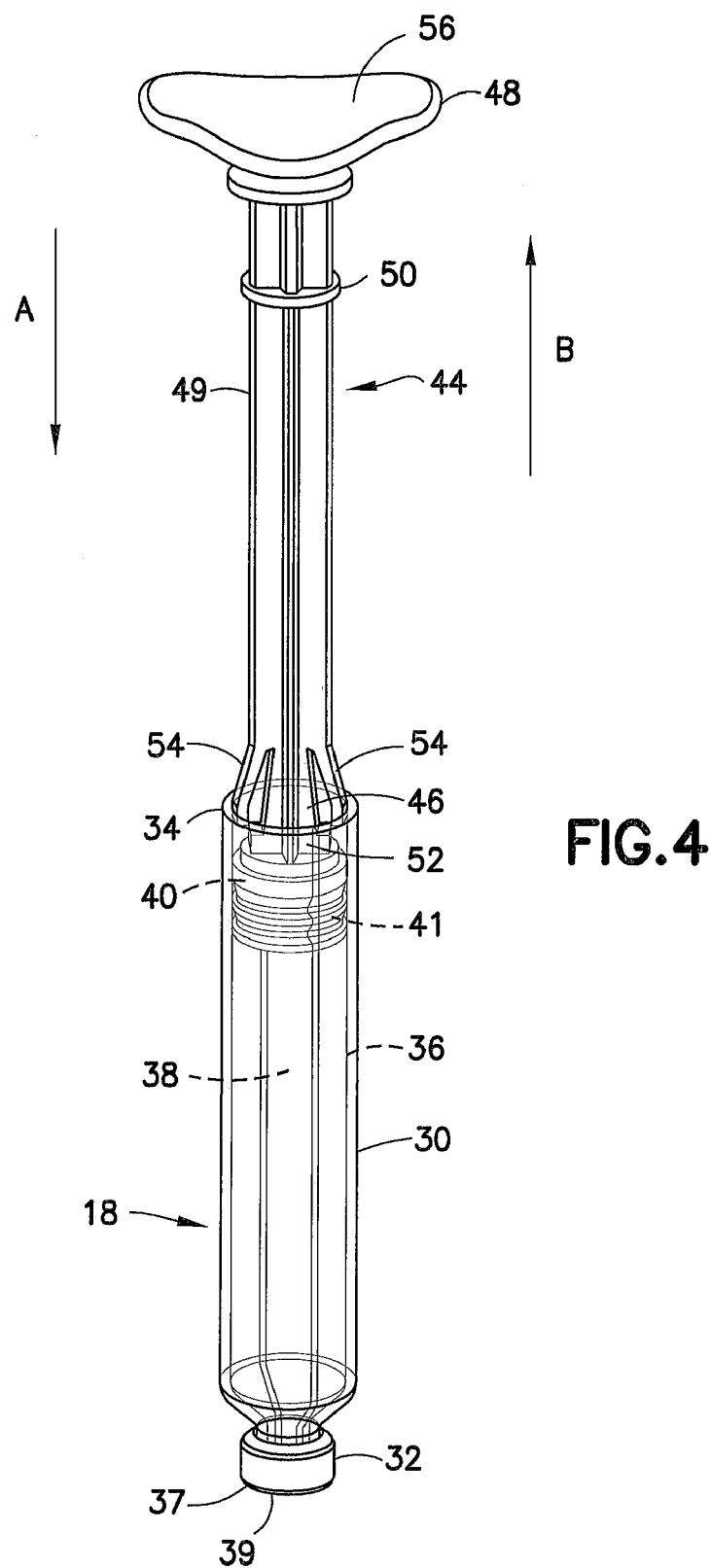
FIG. 4 is an assembled perspective view of a cartridge, a stopper, and a plunger rod of the drug reconstitution system of FIG. 1 in accordance with an embodiment of the present invention.
Figure 5:
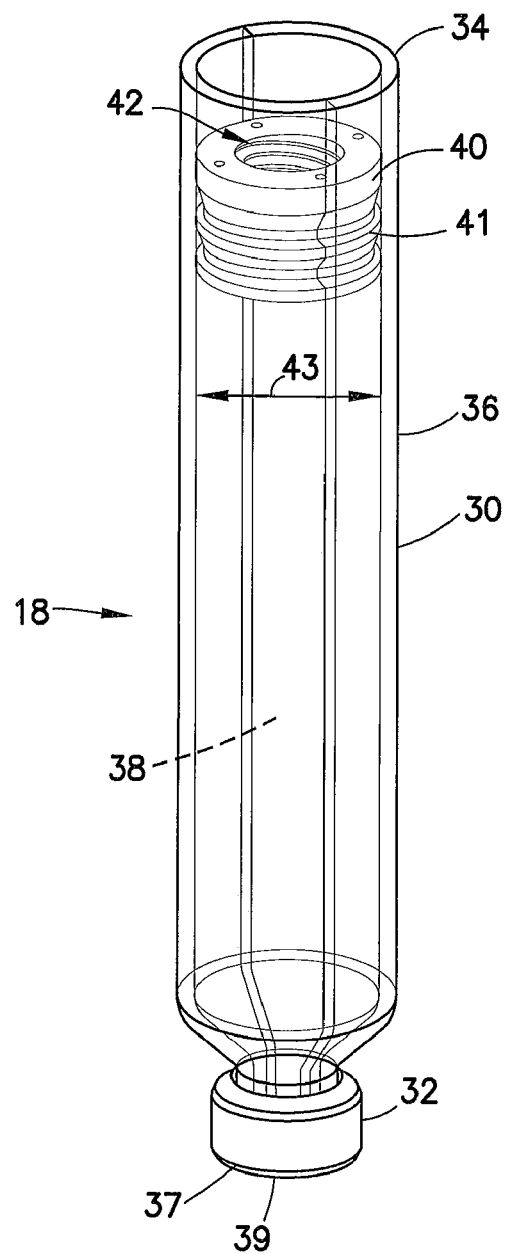
FIG. 5 is a perspective view of the cartridge and the stopper of FIG. 4 in accordance with an embodiment of the present invention.
Figure 6:
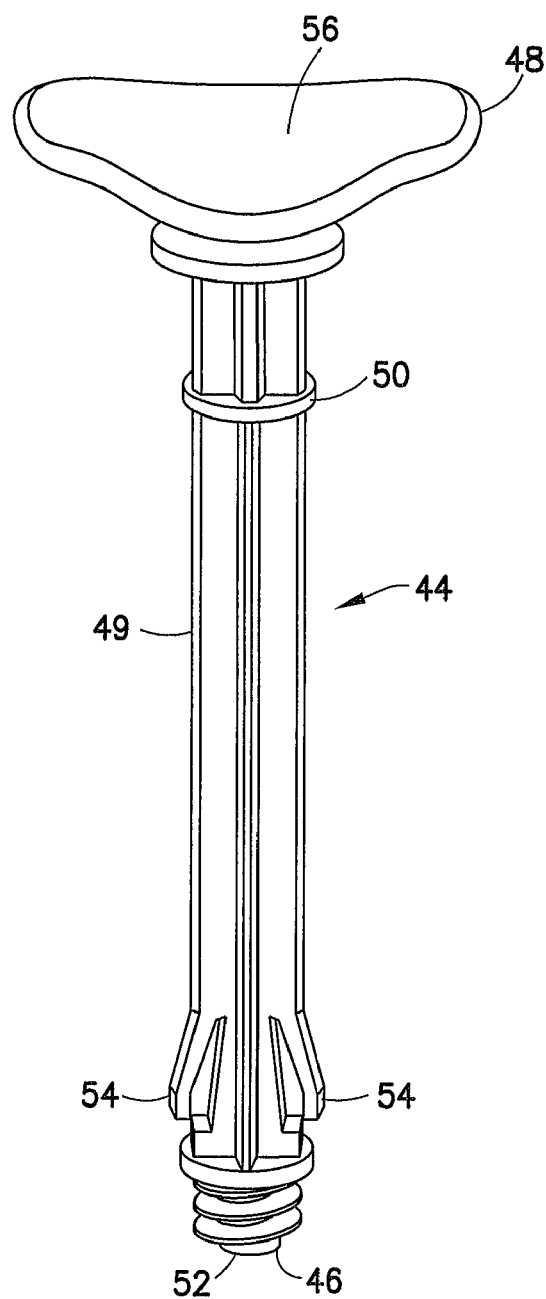
FIG. 6 is a perspective view of the plunger rod of FIG. 4 in accordance with an embodiment of the present invention.

Referring to FIGS. 4 and 5, cartridge 18 includes stopper 40 which is moveably or slidably disposed within interior chamber 38 of cartridge 18, and in sealing contact with the internal surface of sidewall 36 of barrel 30. Stopper 40 is sized relative to barrel 30 to provide sealing engagement with the interior surface of sidewall 36 of barrel 30. Additionally, stopper 40 may include one or more annular ribs 41 extending around the periphery of stopper 40 to increase the sealing engagement between stopper 40 and the interior surface of sidewall 36 of barrel 30. In alternate embodiments, a singular O-ring or a plurality of O-rings may be circumferentially disposed about stopper 40 to increase the sealing engagement with the interior surface of sidewall 36. Referring to FIGS. 4, 5, 21, and 24, stopper 40 also includes a plunger connection portion 42 for securing a plunger rod 44 to stopper 40. In one embodiment, plunger connection portion 42 includes a threaded portion.

Referring to FIGS. 1-4 and 6, cartridge 18 further includes plunger rod 44 which provides a mechanism or actuation member for dispensing fluid, such as a first substance, contained within interior chamber 38 of barrel 30 through outlet opening 39 upon connection of barrel 30 with adapter assembly 14 as will be described in more detail below. Plunger rod 44 is adapted for advancing stopper 40. In one embodiment, plunger rod 44 is sized for movement within interior chamber 38 of barrel 30, and generally includes a first or distal end 46, a second or proximal end 48, a plunger rod body 49 extending between distal end 46 and proximal end 48, a protruding member or protrusion 50 extending from plunger rod 44 adjacent plunger rod proximal end 48, a securement feature or stopper connection portion 52 for securing plunger rod 44 to stopper 40, a deformable restraining member or flexible arms 54 disposed adjacent plunger rod distal end 46, and thumb press or flange portion 56 disposed adjacent plunger rod proximal end 48. Plunger rod 44 provides a mechanism for actuation of stopper 40 between a first position adjacent cartridge proximal end 34 and a second position adjacent cartridge distal end 32. Actuation of plunger rod 44, upon the application of a distal force to flange portion 56 of plunger rod 44, to move stopper 40 from the first position to the second position expels fluid from barrel 30.

Figure 2:
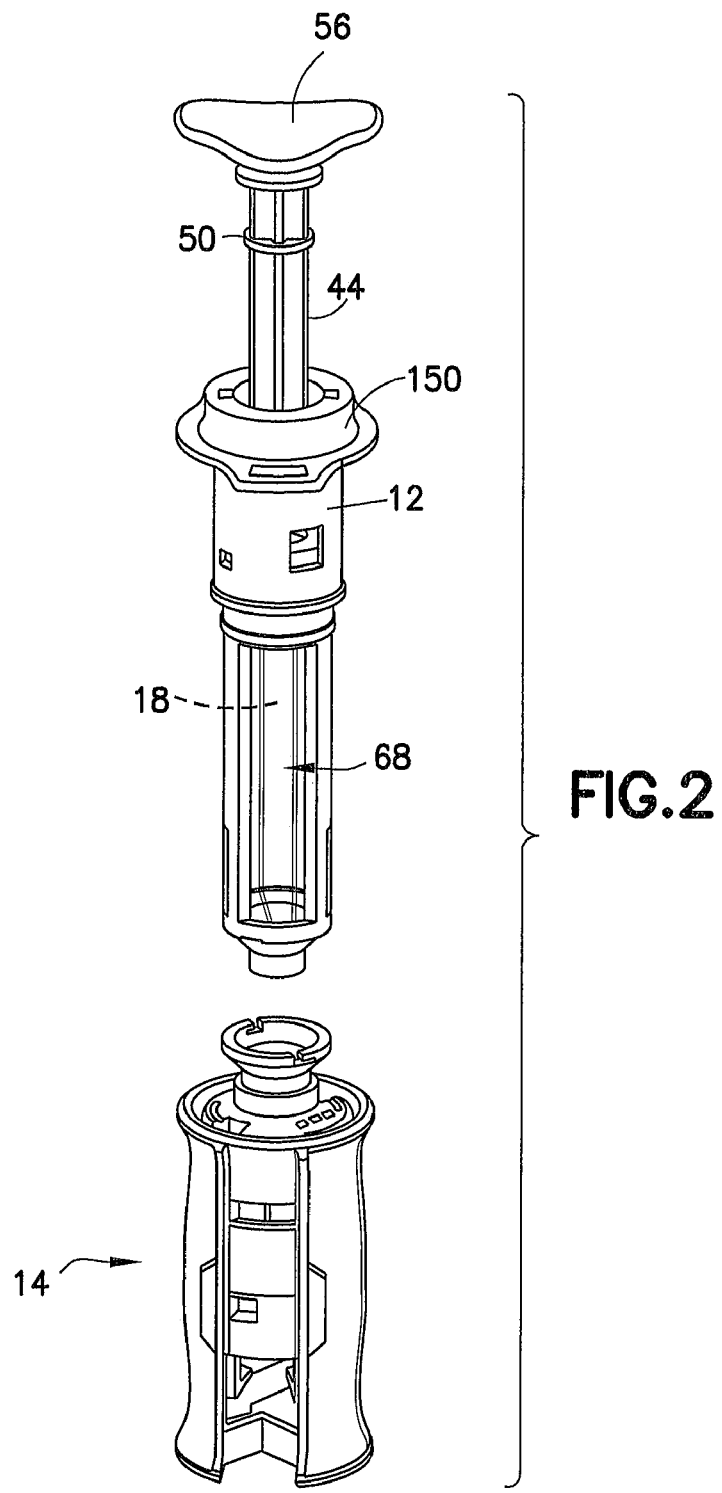
FIG. 2 is an exploded perspective view of a portion of the drug reconstitution system of FIG. 1 in accordance with an embodiment of the present invention.
Figure 3:
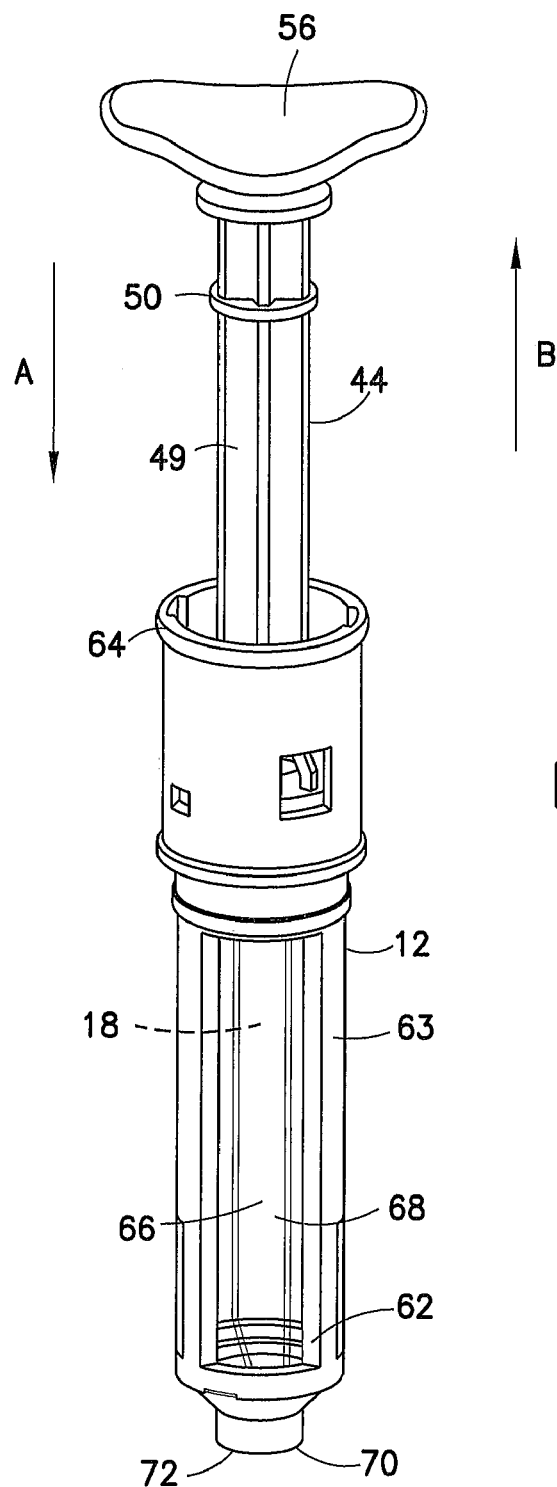
FIG. 3 is an assembled perspective view of a portion of the drug reconstitution system of FIG. 2 in accordance with an embodiment of the present invention.

Referring to FIGS. 1-3, in certain configurations, cartridge 18 includes a cartridge housing 12 having a wall 63 extending between a cartridge housing distal or forward end 62 and a proximal or rearward end 64, thereby defining a cartridge housing interior chamber 66 of cartridge housing 12. Chamber 66 of cartridge housing 12 may be sized and adapted to receive cartridge 18 at least partially therein. In this configuration, cartridge housing 12 may be configured to receive a pre-filled cartridge 18 therein. In other configurations, cartridge 18 may not include exterior cartridge housing 12, and may have the features on the cartridge housing 12 as described herein directly formed on the cartridge 18, as would be found in a unitary construction. Cartridge housing 12 may also include a viewing window 68 allowing a user to view the volume of liquid present in the interior 38 of cartridge 18. At least one of the cartridge tip 37 and/or a tip 70 of cartridge housing 12 is adapted to be engageable with adapter assembly 14. However, in one embodiment, neither of tip 37 nor tip 70 is adapted to be directly engageable with a pen needle normally used with injector 20, as shown in FIG. 1. In this manner, a user is prevented from injecting an un-mixed diluent contained within cartridge 18 to a needle or needle hub for direct injection to the user as there is no place to attach a needle for injection. In such an embodiment, cartridge 18 is only able to be useable by the needle or needle hub used with the injector 20 after cartridge 18 and/or cartridge housing 12, with at least a portion of cartridge 18 contained therein, has been engaged with adapter assembly 14 so that the first substance contained within chamber 38 of cartridge 18 may be expelled to vial chamber 60 via adapter assembly 14, mixed with the second substance contained within vial chamber 60, and the mixture of the first and second substances returned back to barrel 30 of cartridge 18 via adapter assembly 14. A pen needle preferably cannot be attached to the cartridge 18 and/or cartridge housing 12 until needle adapter 82, shown and described with reference to FIGS. 7-12, has been transferred to the cartridge holder 12. In one embodiment, all of the components of cartridge housing 12 may be constructed of any known material, and are desirably constructed of medical grade polymers.

Adapter assembly 14 is provided in removable engagement with tip 37 of cartridge 18 and/or tip 70 of cartridge housing 12. Adapter assembly 14 allows for cartridge 18 and cartridge housing 12 to be coupled in fluid communication with vial 16. In this manner, with vial 16 engaged with adapter assembly 14 and cartridge 18 engaged with adapter assembly 14, interior chamber 38 of cartridge 18 may be in fluid communication with vial chamber 60 of vial 16 via adapter assembly 14.

Referring to FIG. 1, vial 16 may be a standard drug vial of any type having an open head portion covered by a pierceable septum of an elastomeric material. The walls of vial 16 define vial chamber 60 for containing a substance. Drug vial 16 contains the second component of the drug to be reconstituted. The second drug component may be provided in powdered or granular form (e.g., a lyophilized powder). Alternatively, the second component is provided in a wet form, such as a liquid or slurry, for combination with the flowable material in cartridge 18.

Referring to FIGS. 7-12, adapter assembly 14 includes a cylindrical or adapter body 80, a needle adapter 82, a slider 84, a needle holder 86, and a needle 88. Adapter assembly 14 is adapted to contain structure that provides for sequential engagement first with vial 16 and second with cartridge 18. In this manner, liquid contained within chamber 38 of cartridge 18 is prevented from dripping out of adapter assembly 14 with no vial engaged to adapter assembly 14 to receive the liquid.

Figure 7:
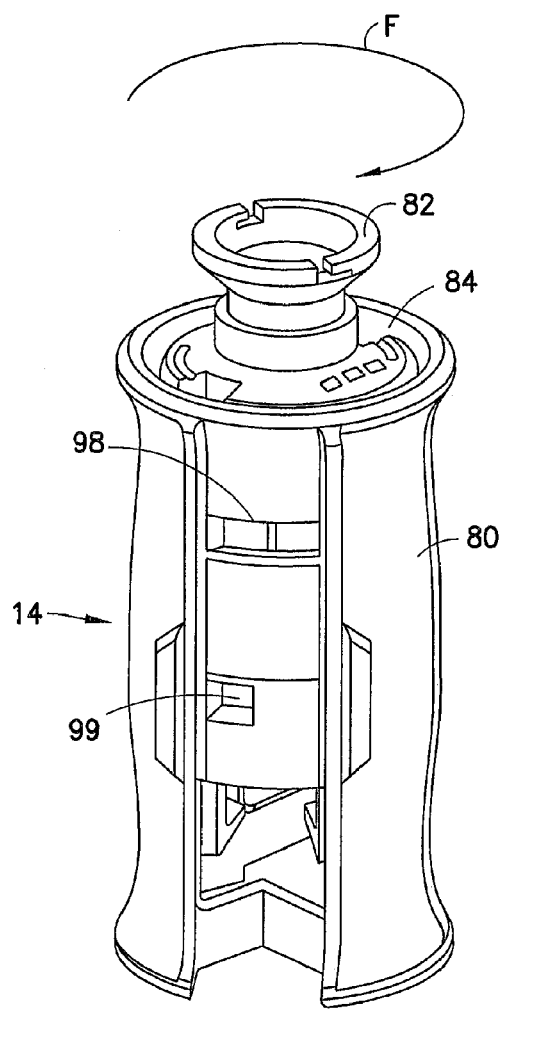
FIG. 7 is a perspective view of an adapter assembly of the drug reconstitution system of FIG. 1 in accordance with an embodiment of the present invention.
Figure 8:
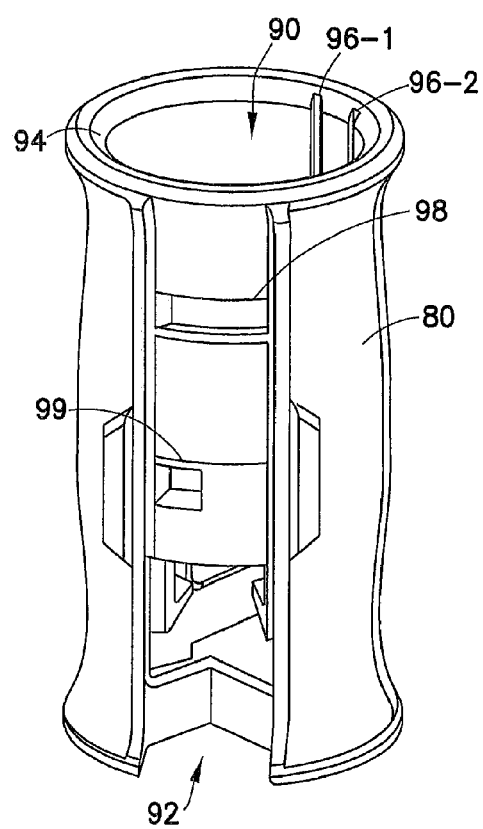
FIG. 8 is a perspective view of an adapter body of the adapter assembly of FIG. 7 in accordance with an embodiment of the present invention.

Referring to FIGS. 7 and 8, adapter body 80 defines a hollow passage 90 therethrough. Adapter body 80 also includes a vial receiving portion 92 that is adapted to engage vial 16 at a first end of adapter body 80 and a cartridge holder receiving portion 94 that is adapted to engage cartridge 18 and/or cartridge housing 12 at an opposite end of adapter body 80.

Figure 9:
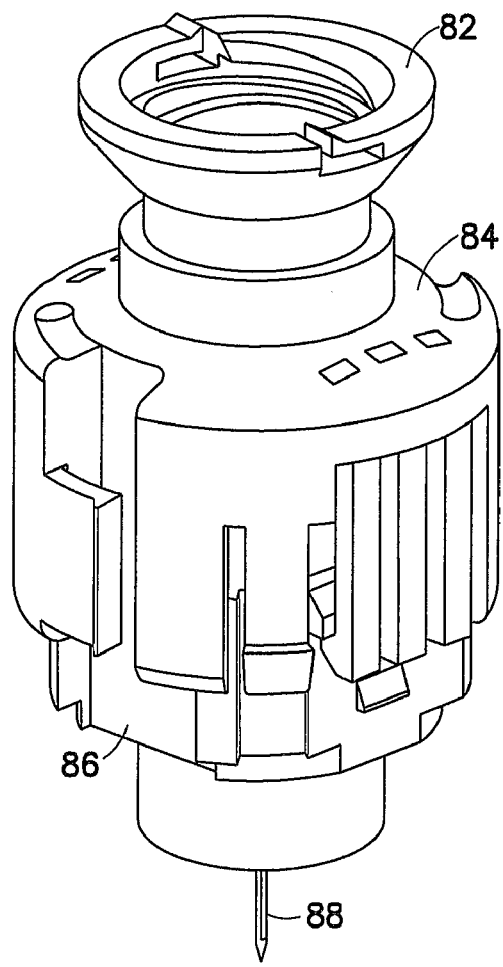
FIG. 9 is an assembled perspective view of a needle adapter, a slider, and a needle holder of the adapter assembly of FIG. 7 in accordance with an embodiment of the present invention.
Figure 10:
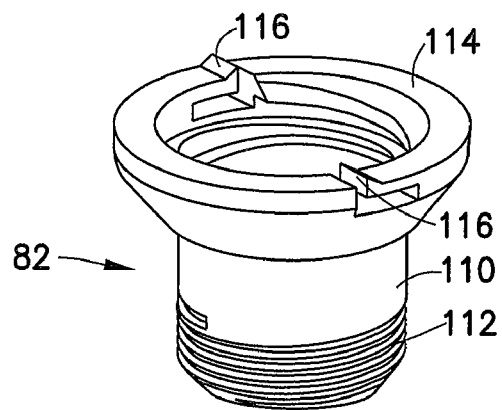
FIG. 10 is a perspective view of the needle adapter of FIG. 9 in accordance with an embodiment of the present invention.
Figure 11:
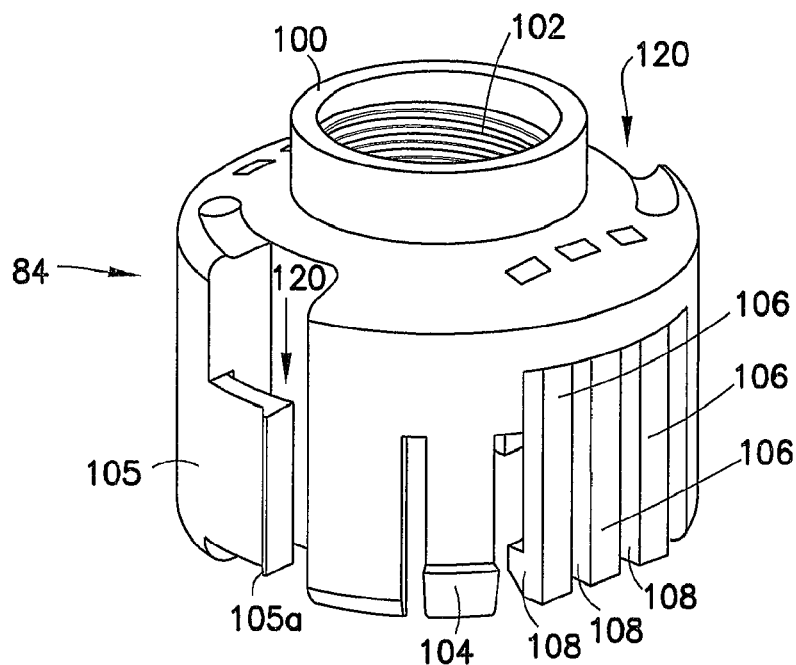
FIG. 11 is a perspective view of the slider of FIG. 9 in accordance with an embodiment of the present invention.

Referring to FIGS. 7, 9, and 11, adapter assembly includes slider 84, such as a slidable adapter, that is adapted to slide longitudinally along a portion of hollow passage 90 of adapter body 80. Slider 84 also includes an engagement or connection end 100, such as a threaded portion 102, that is provided on or within a top portion of slider 84 for connecting slider 84, in one embodiment, to cartridge housing 12, such as by corresponding threaded engagement. In another embodiment, connection end 100 of slider 84, as shown in FIGS. 7 and 9, is adapted to connect to needle adapter 82, as shown in FIG. 10.

Referring to FIG. 10, needle adapter 82 includes a needle or slider connection portion 110, such as a threaded portion 112, at a first end and a cartridge housing connection portion 114 including locking tabs 116 at an opposing second end. This threaded portion 112 may be provided with corresponding threads for engagement with the threaded portion of a pen needle. As shown in FIGS. 7 and 9, needle adapter 82 is engageable with slider 84 via engagement of slider connection portion 110 of needle adapter 82 and connector end 100 of slider 84. Cartridge housing 12 and/or cartridge 18 may be received at least partially therein and connectable to adapter assembly 14 via cartridge housing connection portion 114 of needle adapter 82. With cartridge housing 12 connected to cartridge housing connection portion 114, after a first substance or liquid contained within chamber 38 of cartridge 18 has been expelled and mixed with a second substance or powder contained within vial 16 and the mixture of substances transferred back into chamber 38 of cartridge 18 via adapter assembly 14, rotation of cartridge housing 12 while connected to adapter assembly 14 causes locking tabs 116 to engage cartridge housing 12. In this manner, upon removal of cartridge housing 12 from adapter assembly 14, needle adapter 82 is connected to cartridge housing 12 which contains cartridge 18 including the mixture of the substances.

Once needle adapter 82 has been transferred to cartridge housing 12, a user may then secure cartridge housing 12 containing cartridge 18 to injector 20 by connecting housing distal end to a connection portion of injector 20. Needle connection portion 110 of needle adapter 82 is adapted to be attached to injector 20 while tip 37 of cartridge 18 is not engageable with injector 20. In this manner, a user is prevented from accidently securing cartridge 18 containing a pre-reconstituted composition to the injector 20 for injection to the body of the user.

Figure 27:
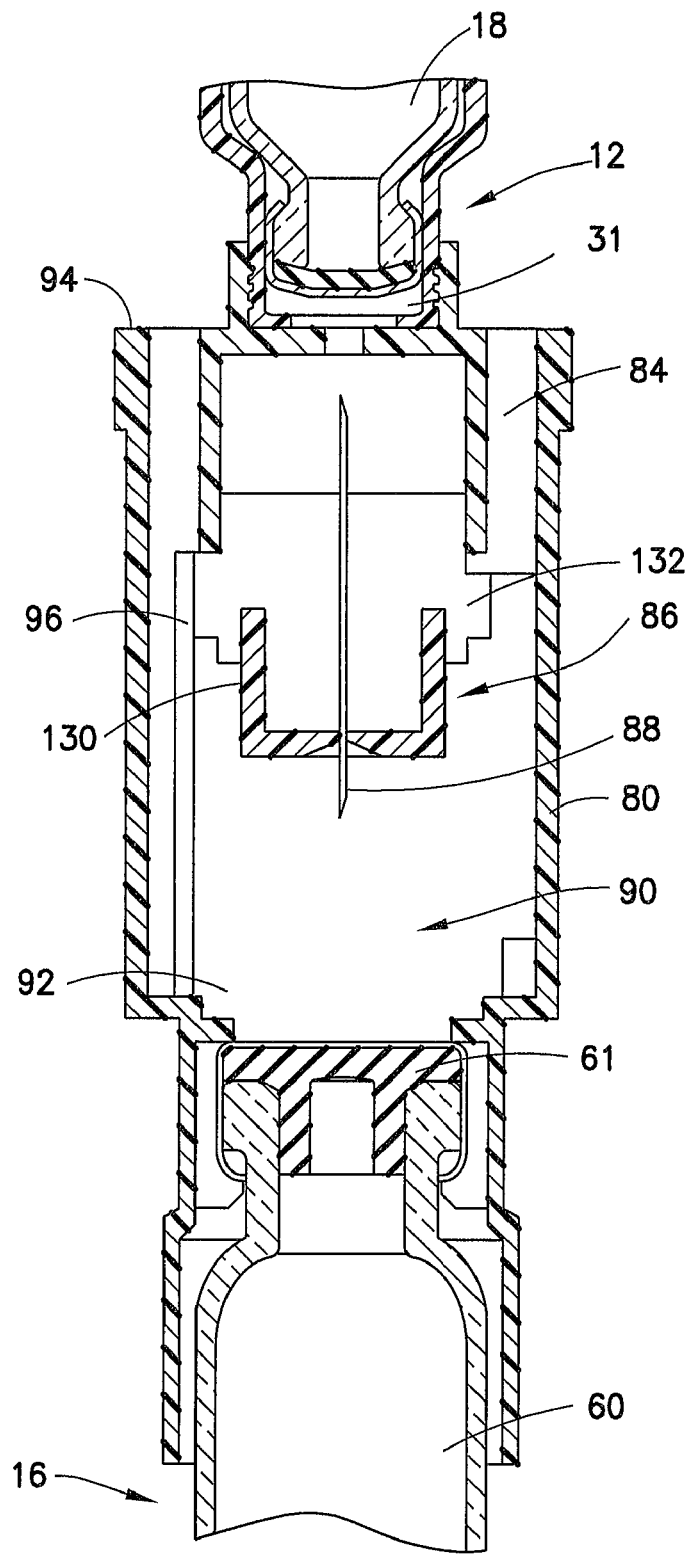
FIG. 27 is a partial cross-sectional view of the adapter assembly of the drug reconstitution system of FIG. 1 with the slider and the needle holder in an initial position in accordance with an embodiment of the present invention.
Figure 28:
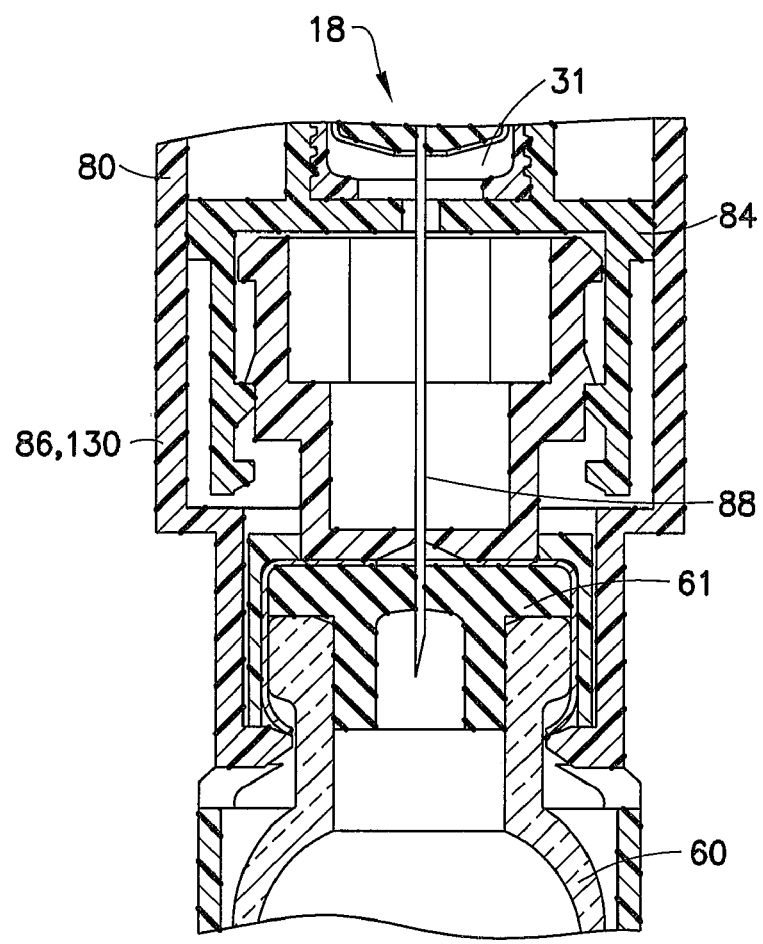
FIG. 28 is a partial cross-sectional view of the adapter assembly of the drug reconstitution system of FIG. 1 in which the slider and the needle holder have moved to a final position and in which the needle has punctured the septum of both the cartridge and the vial in accordance with an embodiment of the present invention.

As shown in FIG. 8, grooves 96-1 and 96-2 are included on the interior walls in hollow passage 90 of adapter body 80. Grooves 96-1 and 96-2 support slider 84 which is movable from an initial position, in which slider 84 is disposed adjacent cartridge holder receiving portion 94 of adapter body 80 as shown in FIG. 27, to a final position in which slider 84 is disposed adjacent vial receiving portion 92, as shown in FIG. 8, of adapter body 80 as shown in FIG. 28.

Referring to FIG. 11, slider 84 includes a locking tab 104 which is engagable with a riser slot 98, as shown in FIG. 8, defined within or connected to a portion of adapter body 80 and which holds slider 84 in the initial position until adapter body 80 is twisted. Twisting adapter body 80 in the direction of arrow F, as shown in FIG. 7, forces a ratchet 105, as shown in FIG. 11, specifically a ratchet surface 105a, to pass from groove 96-1 to groove 96-2, as shown in FIG. 8, thereby releasing slider 84 and allowing slider 84 to move longitudinally within adapter body 80. In effect, ratchet 105 and groove 96-1 offers torque resistance requiring the user to provide sufficient rotational (e.g., twisting) force before slider 84 is released and can be moved from the initial position shown in FIG. 27 to the final position shown in FIG. 28.

Figure 29:
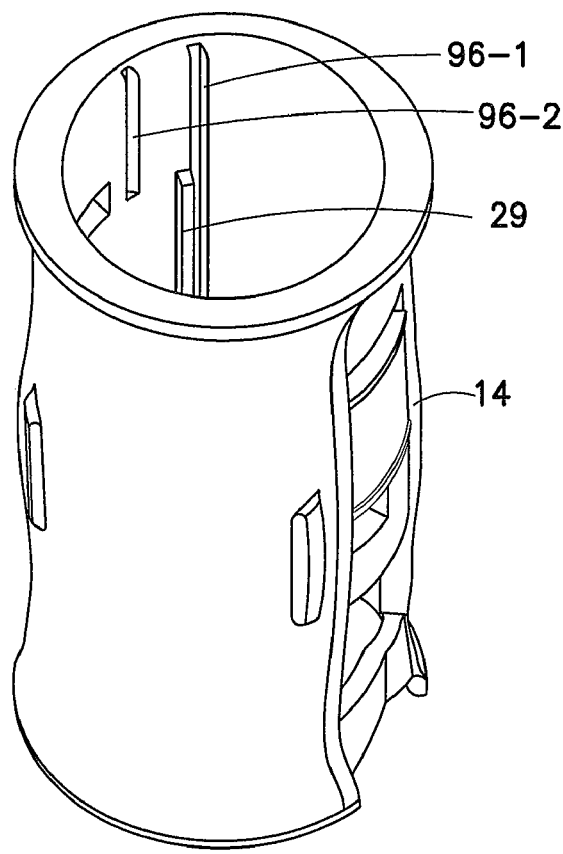
FIG. 29 is a perspective view of the adapter of FIG. 1 in accordance with an embodiment of the present invention.
Figure 30:
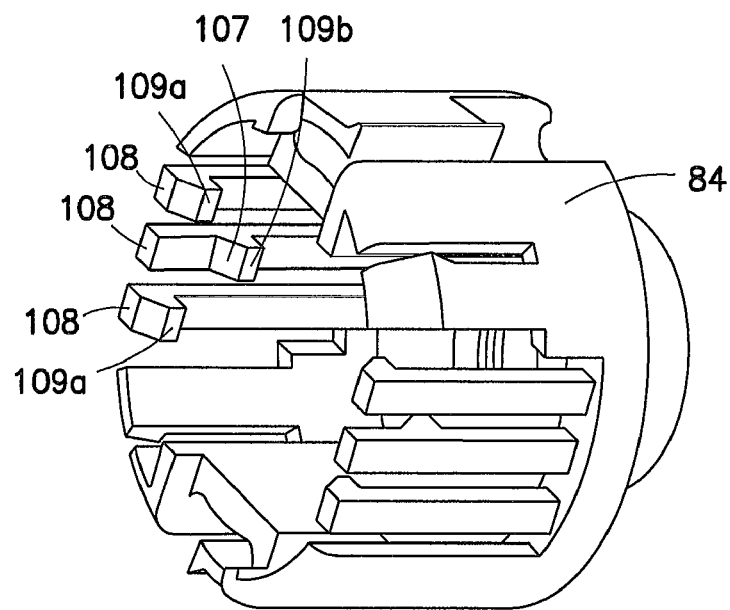
FIG. 30 is a perspective view of the slider of FIG. 11 in accordance with an embodiment of the present invention.

Referring to FIG. 11, slider 84 includes a plurality of push fingers 106 which are attached to the body of slider 84. Latch ends or assembly supports 108 are located at the free end of each of the push fingers 106. Slider 84 further includes guide channels 120 for receiving a guide rib 96, as shown in FIG. 29, located on the interior of hollow chamber or passage 90 of adapter body 80. As shown in FIGS. 27 and 28, push fingers 106 are adapted to contact, but not connect, with needle holder 86 (see also FIGS. 9 and 12). Needle holder 86 includes a dual tipped needle 88 and a supporting structure 130. Supporting structure 130 includes a slide ledge 132. Referring to FIG. 30, ledge 132, shown in FIG. 12, contacts engaging surface 107 of the needle holder 86 until the needle holder 86 encounters resistance. At that time, finger tabs 109 of latch ends 108 deflect outwardly and allow the needle holder 86 to move upwards. Ledge 132 becomes clamped between finger tabs 109*a* and finger tab 109*b* forcing needle holder 86 to longitudinally advance through hollow chamber 90 of adapter body 80 of adapter assembly 14. Support structure 130 of needle holder 86 also includes a needle locking tab 134 extending from the side of needle holder 86 for securing needle holder 86 and needle 88 to slider 84 when slider 84 is in the final (e.g., end of use) position. In this manner, needle holder 86 and needle 88 are prevented from being removed from adapter assembly 14 once fluid communication is established between cartridge 18 and vial 16.

Figure 25:
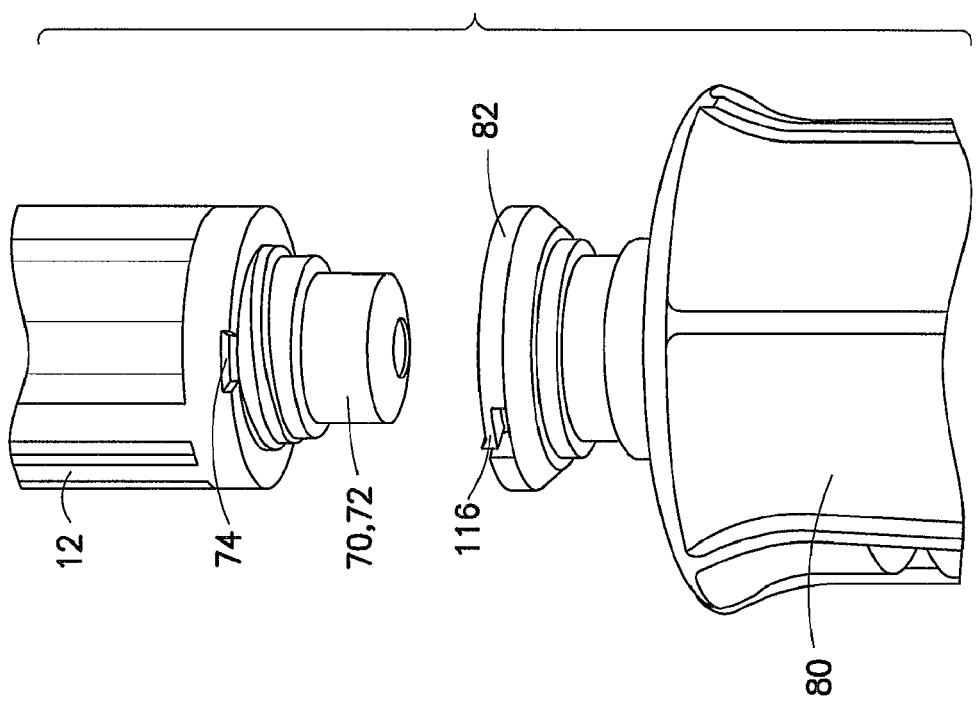
FIG. 25 is an exploded, perspective view of an adapter connection portion and a cartridge distal end of the drug reconstitution system of FIG. 1 in accordance with an embodiment of the present invention.

In use, drug reconstitution system 10 of the present invention is assembled by sequentially or first attaching vial 16 to one end of adapter assembly 14, for example, vial receiving portion 92 of adapter body 80. Next, referring to FIGS. 2 and 25, cartridge housing 12 is attached to the opposite end of adapter assembly 14 by engaging a connection portion 72, such as a male threaded connection, as shown in FIG. 3, of cartridge housing 12 to the corresponding cartridge housing connection portion 114, such as a corresponding female threaded portion, of needle adapter 82 of adapter assembly 14. Connection portion 72 of cartridge housing 12 includes a locking latch 74, as shown in FIG. 25, which is adapted to cooperate with locking tabs 116 of needle adapter 82. For example, with cartridge housing 12 connected to cartridge housing connection portion 114 of needle adapter 82, after a first substance or liquid contained within chamber 38 of cartridge 18 has been expelled and mixed with a second substance or powder contained within vial 16 via adapter assembly 14 and the mixture of substances transferred back into chamber 38 of cartridge 18 via adapter assembly 14, rotation of cartridge housing 12 while connected to adapter assembly 14 via needle adapter 82 causes locking tabs 116 to engage locking latches 74 of cartridge housing 12. In this manner, upon removal of cartridge housing 12 from adapter assembly 14, needle adapter 82 is connected to cartridge housing 12 which contains cartridge 18 including the mixture of the substances. Subsequently, a user may then secure cartridge housing 12 containing cartridge 18 to injector 20 and connect a pen to the needle connection portion 110 of needle adapter 82 to a connection portion of injector 20, such as by threaded connection. In certain configurations, the connection portion 72 may include a half turned threaded profile which does not correspond to the threaded profile of the injector 20. Accordingly, in this manner, a user is prevented from accidently securing cartridge housing 12 containing cartridge 18 which includes a liquid to the injector 20 for injection to the body of the user as these threaded profiles do not correspondingly engage.

In one embodiment, drug reconstitution system 10 is provided as a pre-assembled kit in which cartridge housing 12, cartridge 18, and vial 16 are connected to adapter assembly 14 but are not yet in fluid communication with one another through needle 88.

Figure 12:
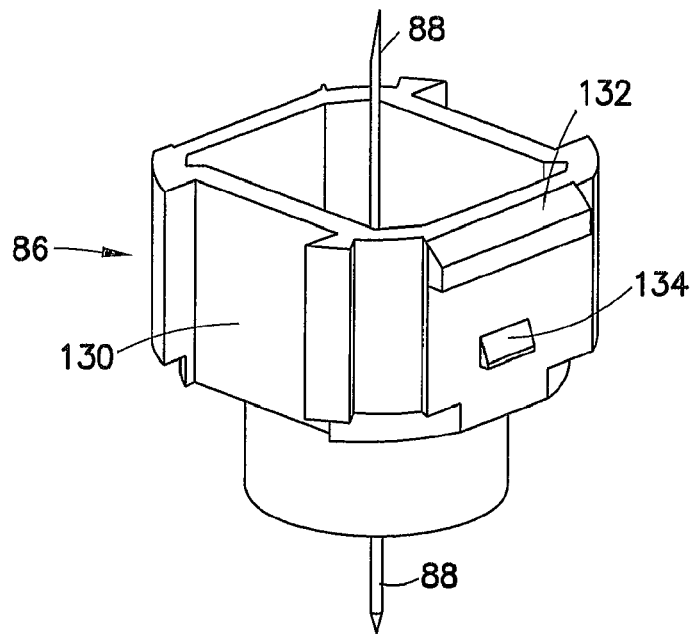
FIG. 12 is a perspective view of the needle holder of FIG. 9 in accordance with an embodiment of the present invention.

Once the cartridge holder 12 and vial 16 are securely connected to adapter assembly 14, system 10 is activated by first twisting then pushing cartridge housing 12 towards vial 16 and twisting adapter body 80 of adapter assembly 14 to release ratchet arm 105. Following activation, the user pushes on cartridge housing 12 to advance slider 84 through adapter body 80. Slider 84 is supported by grooves 96-1 then 96-2 which correspond to guide channels 120 of slider 84 as discussed above. Latch ends 108 of slider 84 contact slide ledge 132 of needle holder 86, thereby pushing needle holder 86 and needle 88 longitudinally along the interior wall of adapter body 80. Continued force on slider 84 causes a vial end of needle 88 to contact and eventually pierce septum 61 of vial 16, as shown in FIG. 28. At this point, locking tab 104 of slider 84 engages with the end of a lock slot 99 (FIGS. 7 and 8), located near vial receiving portion 92 of adapter body 80 to hold slider 84 in this position. Similarly, locking tabs 134 of needle holder 86 engage with corresponding tabs on the interior of slider 84 to secure needle holder 86 in this position. Referring to FIGS. 12 and 30, ledge 132 is seated within finger tabs 109*a* and finger tab 109*b*. In this way, needle holder 86 is prevented from being removed from adapter body 80 exposing needle 88.

Referring to FIG. 28, as the user continues to advance cartridge 18 and cartridge housing 12 by applying force to slider 84, a septum 31 of cartridge 18 is brought into contact with a cartridge end of needle 88. As pressure increases, needle 88 pierces septum 31 of cartridge 18, thereby establishing fluid communication between vial 16 and cartridge 18 through needle 88.

At this point, the user presses down on plunger rod 44 in the direction of arrow A, as shown in FIGS. 3 and 4, advancing stopper 40 within cartridge 18 from the first position to the second position. Stopper 40 expels the liquid from cartridge 18 and into vial 16 via adapter assembly, i.e., needle 88. Once the liquid is entirely injected into the vial, the user may shake system 10 to mix the dry and liquid components of the drug. In some embodiments, mixing may be accomplished in a matter of seconds whereas in other embodiments mixing can take as long as 20 minutes. The user can determine how much fluid has been expelled from cartridge 18 by observing the fluid level through the viewing window 68 of cartridge housing 12. The user also can tell that all fluid has been expelled from cartridge 18 when stopper 40 is at the base of cartridge 18 and plunger rod 44 cannot be further advanced. The amount of mixing required is based on the composition, solubility, and viscosity of the dry and liquid components initially present in vial 16 and cartridge 18 to be reconstituted.

Figure 19:
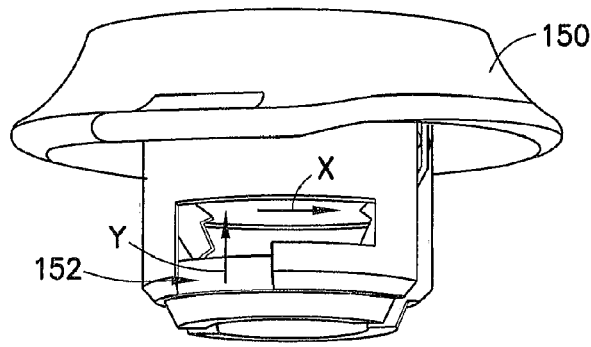
FIG. 19 is a side perspective view of the latch member of FIG. 17 in accordance with an embodiment of the present invention.
Figure 20:
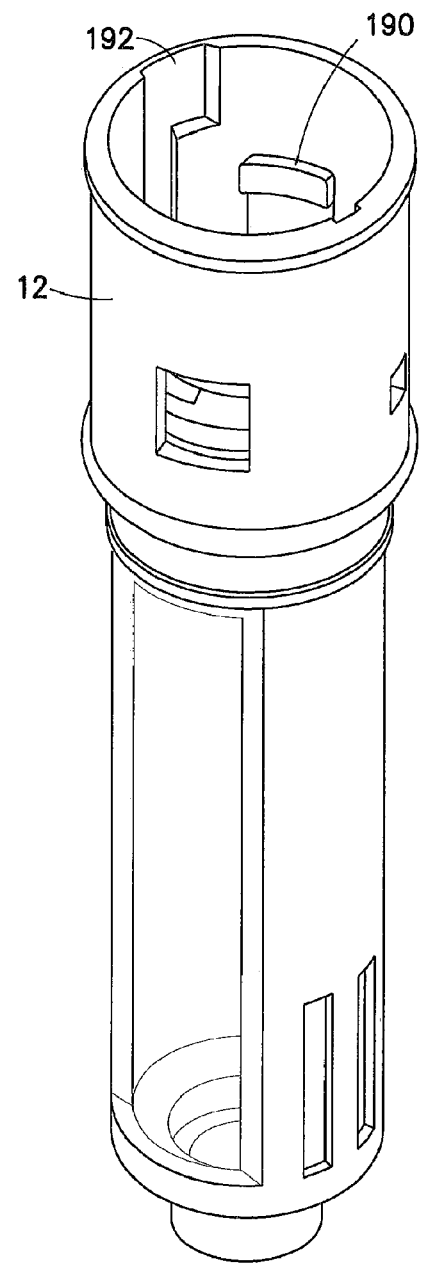
FIG. 20 is a perspective view of the cartridge housing of FIG. 18 in accordance with an embodiment of the present invention.
Figure 21:
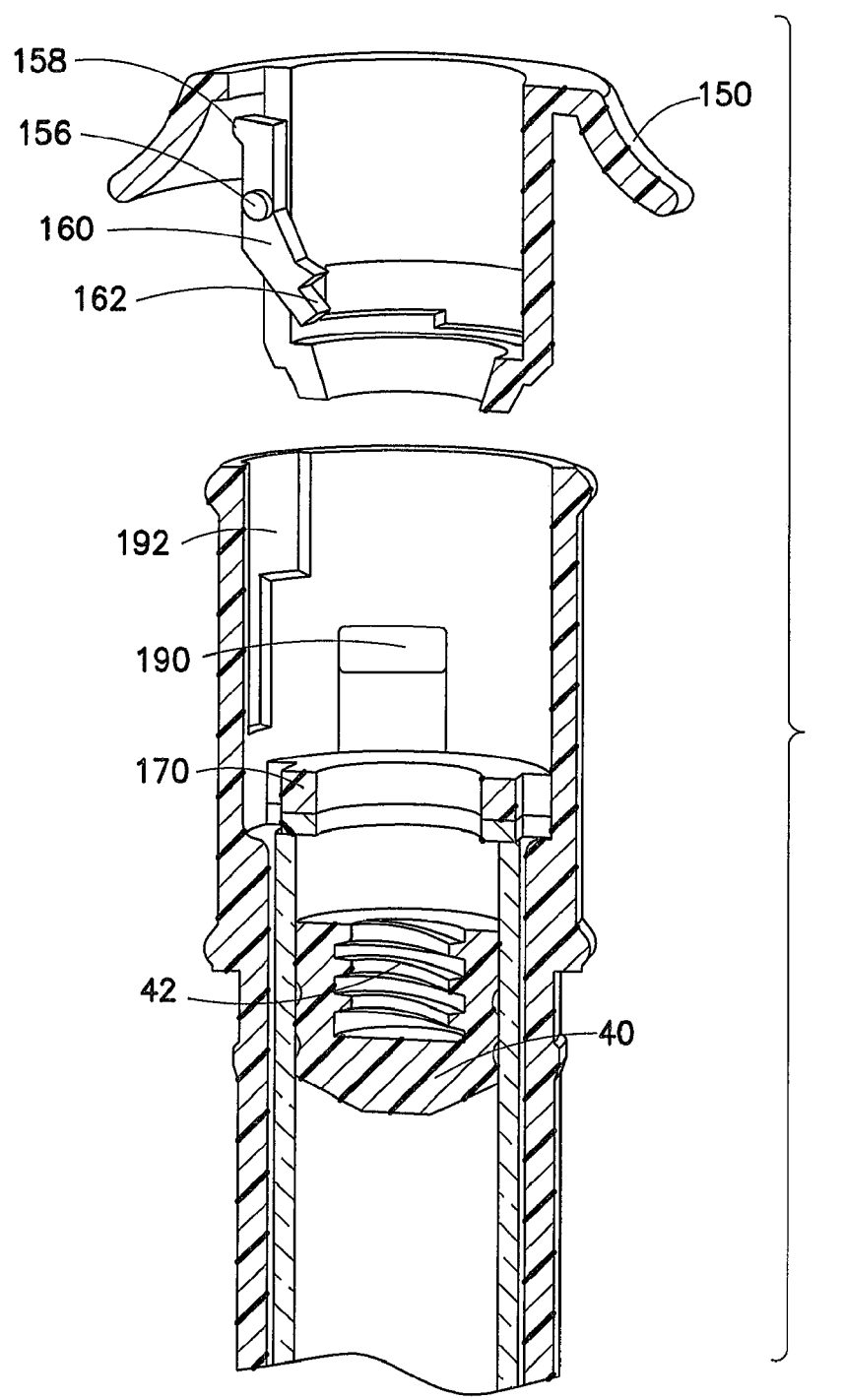
FIG. 21 is an exploded cross-sectional perspective view of the latch member of FIG. 19 and the cartridge housing of FIG. 20 in accordance with an embodiment of the present invention.

In one embodiment, a locking system of the present disclosure allows plunger rod 44 to be in a locked position thereby allowing the user to shake system 10 to mix the dry and liquid components of the drug using only one hand. Referring to FIGS. 15-24, system 10 may include a locking latch or latch member 150 which is engageable with a portion of cartridge housing 12 and a portion of plunger rod 44. Referring to FIGS. 17, 19, 21, and 22, latch member 150 includes opposing bayonet slots 152 and opposing pivoting rockers 154 pivotable relative to latch member 150 via a pivot axis point 156. Rockers 154 each include an upper arm 158 above pivot point 156 and a lower arm 160 below pivot point 156 and including a claw 162. Referring to FIGS. 20 and 21, cartridge housing 12 includes opposing bayonet tabs 190 and a recessed portion 192 on the interior surface of wall 63 of cartridge housing 12.

Figure 22:
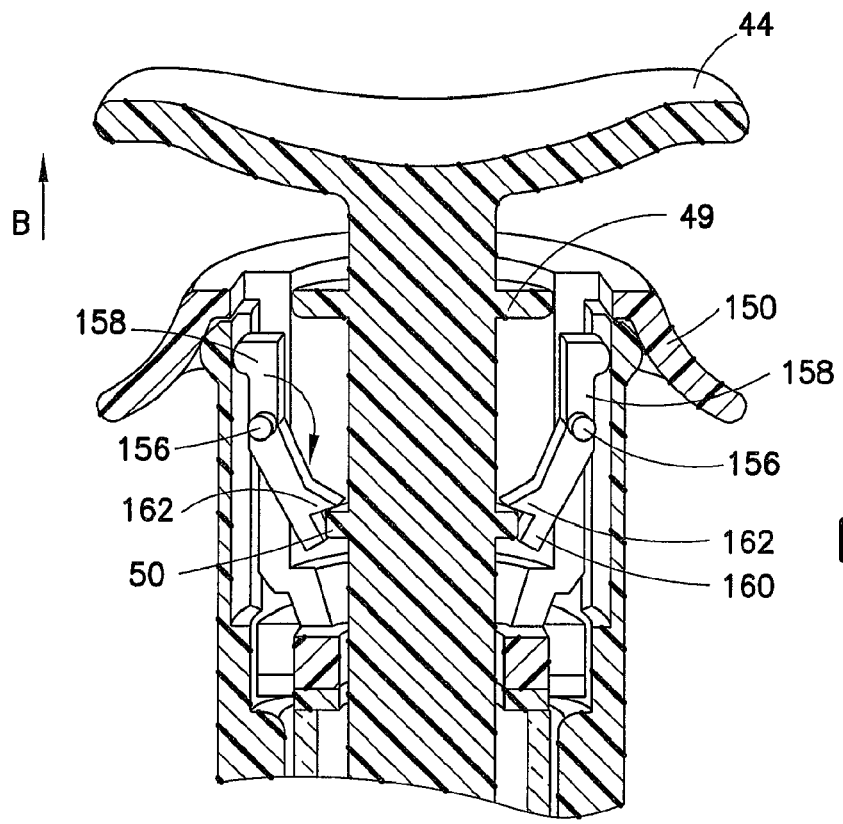
FIG. 22 is an assembled cross-sectional perspective view of FIG. 21 with the plunger rod in a compressed position and including a protrusion of the plunger rod engaged with the latch member in accordance with an embodiment of the present invention.
Figure 23:
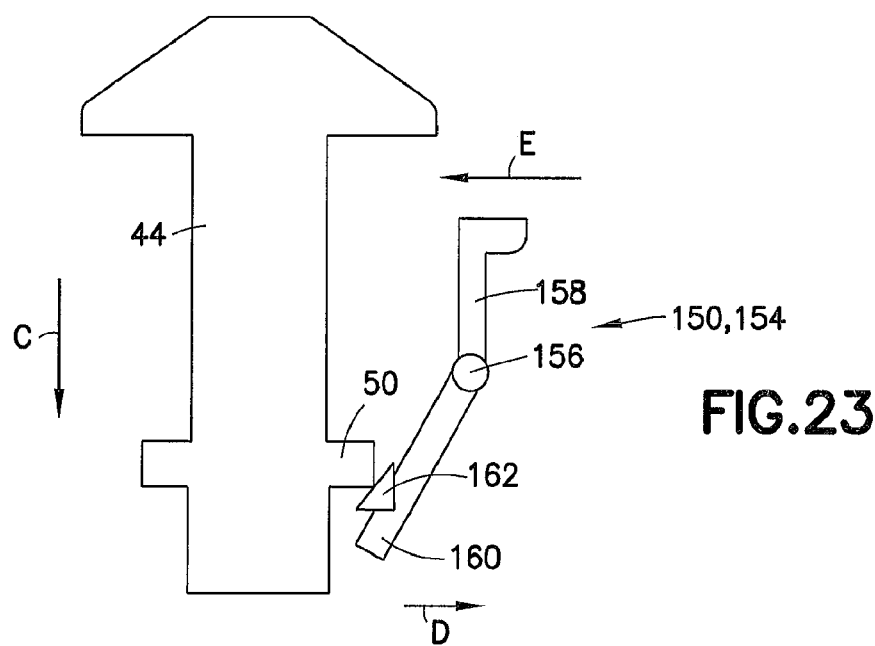
FIG. 23 is a schematic representation of the engagement of the protrusion of the plunger rod with the latch member in accordance with an embodiment of the present invention.

In use, latch member 150 is secured or locked to cartridge housing 12 through a mating bayonet connection, i.e., bayonet slot 152 of latch member 150, and is slid over bayonet tab 190 on cartridge housing 12. Once tab 190 of cartridge housing 12 is disposed within slot 152 of latch member 150, latch member 150 is rotated relative to cartridge housing 12 so that tab 190 of cartridge housing 12 locks within slot 152, as shown in FIG. 19. In use, bayonet tab 190 is directed first vertically along the direction of arrow Y, as shown in FIG. 19, then horizontally along the direction of arrow X. Rotation of latch member 150 to lock on to cartridge housing 12 also forces upper arm 158 of latch member 150 into recessed portion 192 of cartridge housing 12 as shown in FIGS. 20 and 21. In this manner, latch member 150 is locked to cartridge housing 12 and a user is prevented from removing latch member 150 unless plunger rod 44 is actuated in accordance with the present disclosure as will now be discussed. The unlocking of latch member 150 from cartridge housing 12 is only possible when plunger rod 44 is used to actuate stopper 40 from a first position, in which stopper 40 is located adjacent cartridge proximal end 34 (and a first substance is contained within chamber 38 of cartridge 18), to a second position, in which stopper 40 is located adjacent cartridge distal end 32 (and thus the first substance contained within chamber 38 of cartridge 18 is expelled, e.g., to vial chamber 60 via needle 88 for drug mixture). Referring to FIGS. 22 and 23, plunger rod 44 unlocks latch member 150 because as plunger rod 44 is actuated within cartridge housing 12 in a direction generally along arrow C, as shown in FIG. 23, until protrusion 50 of plunger rod 44 engages claw 162 of pivoting rocker 154 of latch member 150 and as protrusion 50 slides over and past claw 162 as shown in FIGS. 22 and 23, protrusion 50 of plunger rod 44 engages claw 162 and forces lower arm. 160 of pivoting rocker 154 in a direction generally along arrow D, as shown in FIG. 23. Actuation of lower arm 160 in the direction generally along arrow D causes upper arm 158 of pivoting rocker 154 to pivot via pivot point 156 in a direction generally along arrow E, as shown in FIG. 23, and thus upper arm 158 pivots out of the locked position within recess 192 of cartridge housing 12. In this manner, the engagement of plunger rod 44 and latch member 150 causes latch member 150 to rotationally unlock (latch member 150 is at this point still axially constrained) from cartridge housing 12 and latch member 150 to lock to plunger rod 44 via claw 162 engaging protrusion 50 of plunger rod 44 as shown in FIG. 22. Advantageously, with latch member 150 locked to plunger rod 44 and latch member 150 axially locked to cartridge housing 12 as shown in FIG. 22, a user may mix the liquid and dry substances now contained in vial 16 by shaking system 10 with one hand.

Next, with upper arm 158 unlocked from recess 192, latch member 150 which is locked to plunger rod 44 can be rotated relative to cartridge housing 12 thus removing bayonet tab 190 of cartridge housing 12 from bayonet slot 152 of latch member 150. In this manner, latch member 150 is completely detached from cartridge housing 12. Next, plunger rod 44 can be used to actuate stopper 40 back from the second position to the first position to draw the mixed drug back into cartridge 18 via a suction force or a vacuum. Actuation of plunger rod 44 back out of cartridge 18 moves latch member 150, which is locked to plunger rod 44, out from cartridge housing 12 as shown in FIG. 24.

Figures 13, 14:
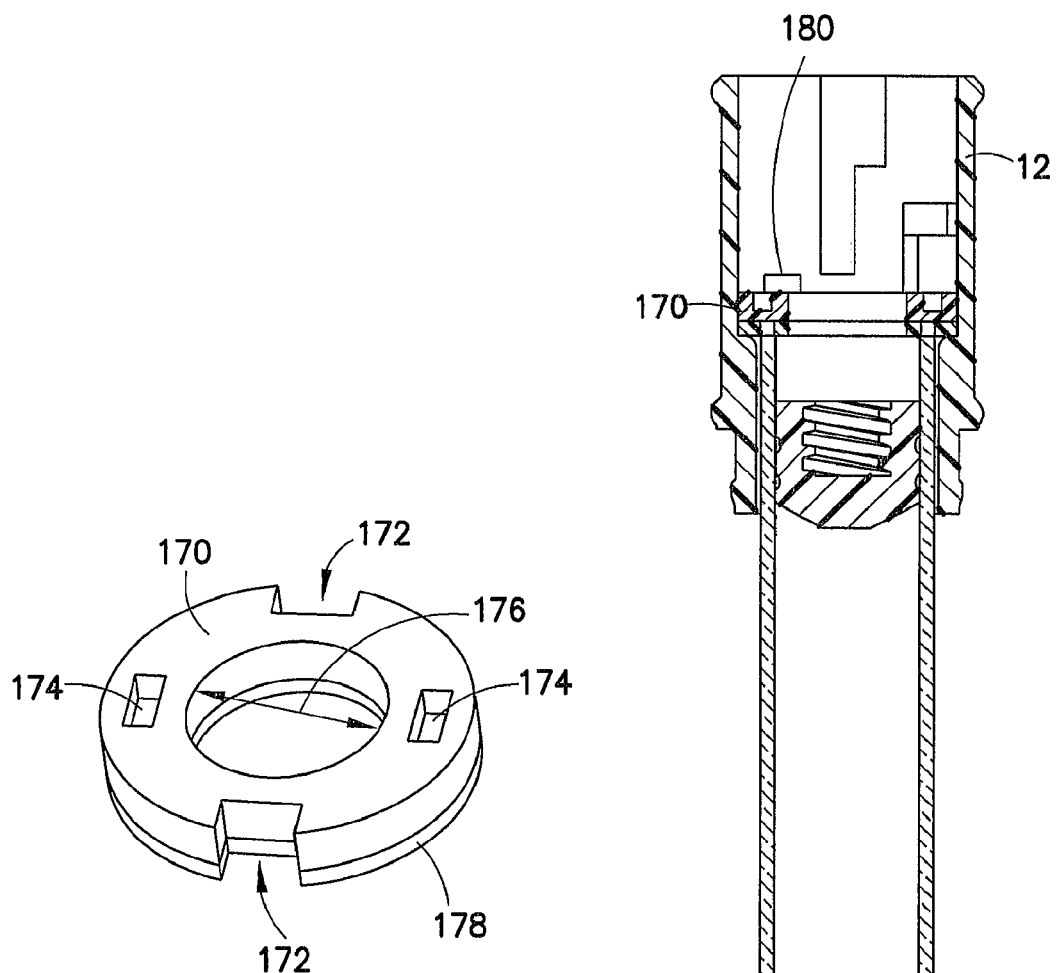
FIG. 13 is a perspective view of a locking member of the drug reconstitution system of FIG. 1 in accordance with an embodiment of the present invention.
FIG. 14 is a cross-sectional view of the locking member of FIG. 13 connected to a cartridge of the drug reconstitution system of FIG. 1 in accordance with an embodiment of the present invention.
Figure 15:
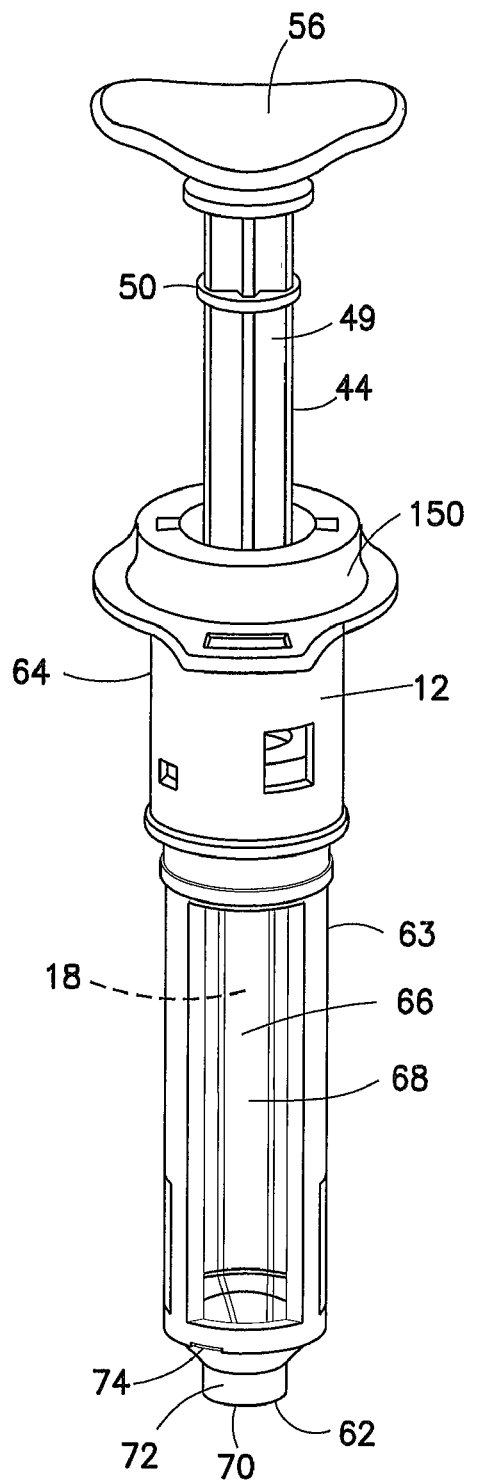
FIG. 15 is an assembled perspective view of a portion of the drug reconstitution system of FIG. 2 in accordance with an embodiment of the present invention.
Figure 16:
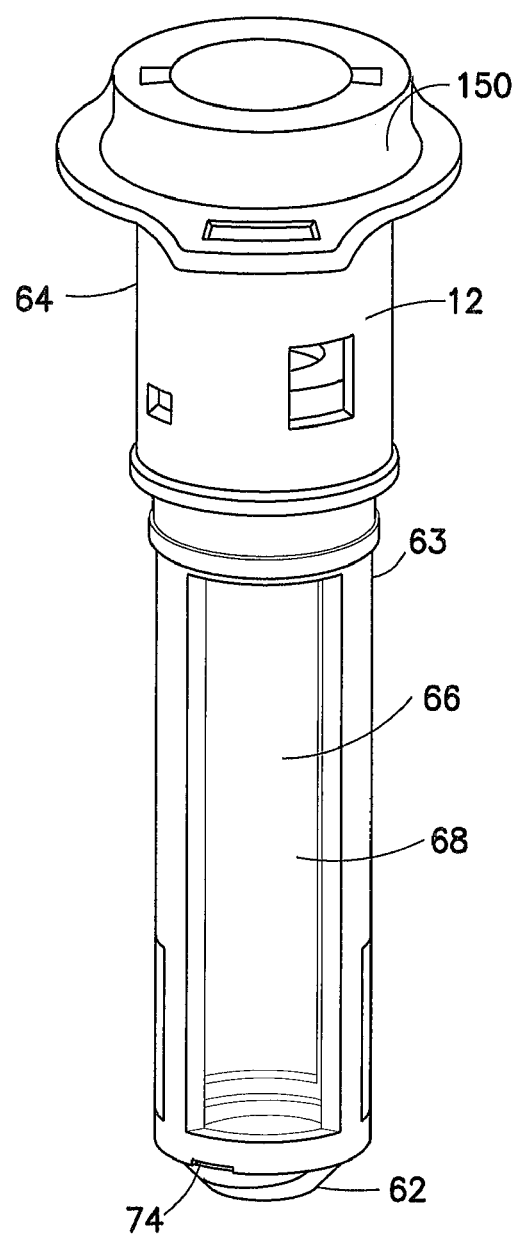
FIG. 16 is a perspective view of the cartridge housing of FIG. 15 including a latch member secured to the cartridge housing in accordance with an embodiment of the present invention.
Figures 17, 18:
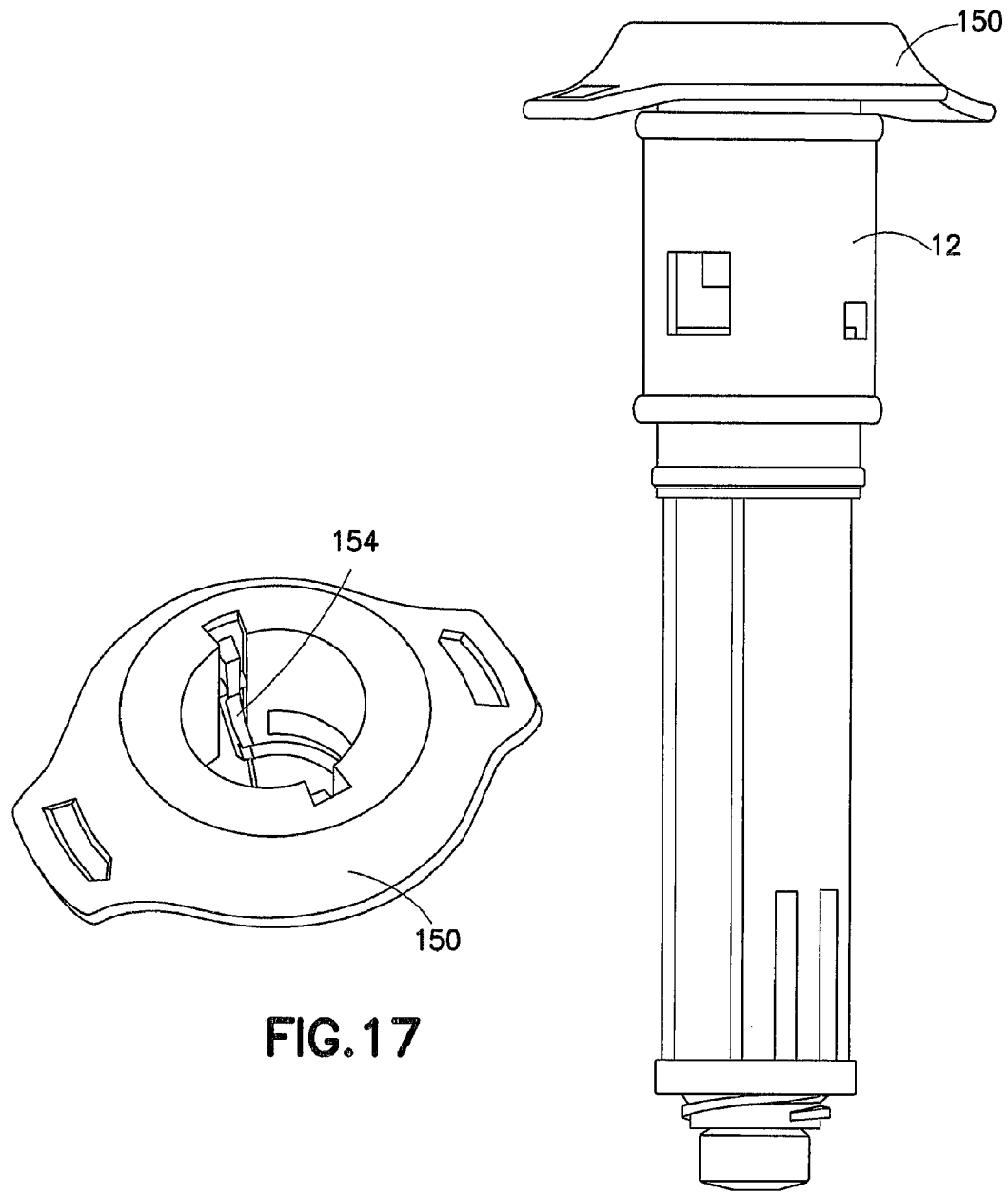
FIG. 17 is a top perspective view of a latch member of the drug reconstitution system of FIG. 1 in accordance with an embodiment of the present invention.
FIG. 18 is a perspective view of the cartridge housing of FIG. 16 including the latch member of FIG. 17 secured to the cartridge housing in accordance with an embodiment of the present invention.

After mixing the substances as described above, the user may invert system 10 and pull plunger rod 44 in a direction generally along arrow B, as shown in FIGS. 3, 4, and 22, away from vial 16 and adapter assembly 14 to draw the mixed drug back into cartridge 18 via suction. Referring to FIGS. 13 and 14, in one embodiment, system 10 includes a locking ring or locking member 170 which is connected to cartridge housing 12 and is adapted to prevent stopper 40 from sliding out of cartridge 18 or being accidently pulled out from cartridge 18 when plunger rod 44 is pulled out from cartridge 18. Referring to FIG. 13, locking member 170 includes opposing slots 172, a top portion of locking member 170 defines opposing receiving channels 174, and locking member 170 defines a locking member inner diameter 176. Referring to FIG. 14, cartridge housing 12 includes locking member tab(s) 180. To secure locking member 170 to cartridge housing 12, locking member 170 is inserted into cartridge housing 12 so that slots 172 are aligned with locking member tabs 180. Next, locking member 170 is pushed into cartridge housing 12 until locking member tabs 180 of cartridge housing 12 are located beyond slots 172 of locking member 170. Then locking member 170 is rotated so that tabs 180 provide a physical barrier abutting a top portion of locking member 170 thereby securing locking member 170 in cartridge housing 12. In one embodiment, a tool may be inserted into receiving channels 174 of locking member 170 to rotate and lock locking member 170 in cartridge housing 12.

With locking member 170 connected to cartridge housing 12 as described above, locking member 170 provides a physical barrier preventing stopper 40 from sliding out of cartridge 18. For example, referring to FIGS. 13, 14, and 24, because locking member inner diameter 176 is less than a stopper outer diameter 43 (FIG. 5), locking member 170 provides a physical barrier preventing stopper 40 from sliding out of cartridge 18.

Figure 24:
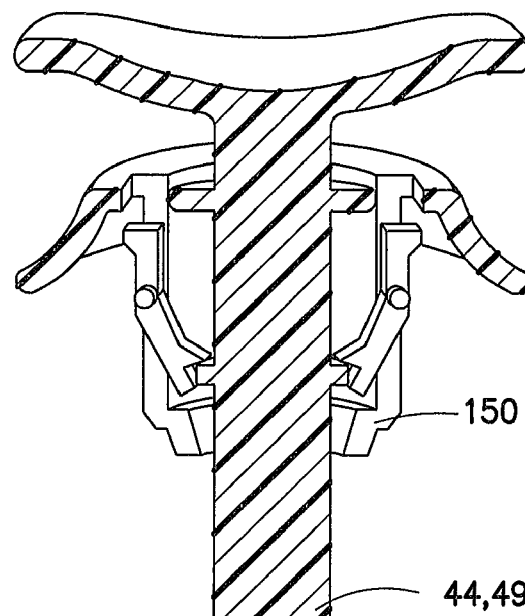
FIG. 24 is an assembled cross-sectional perspective view of FIG. 22 with the plunger rod in a pulled back position and including a protrusion of the plunger rod engaged with the latch member in accordance with an embodiment of the present invention.
Figure 26:
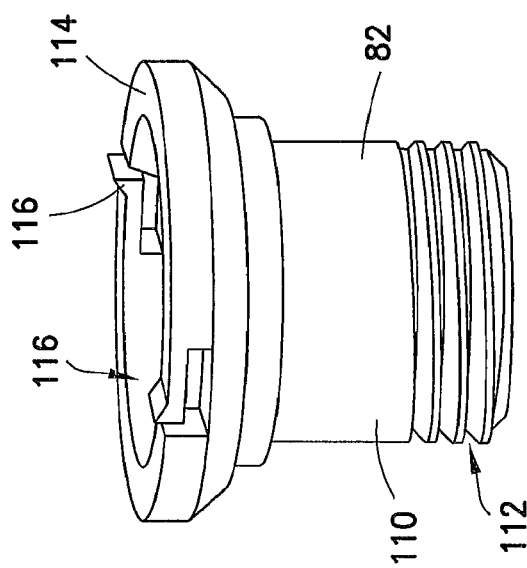
FIG. 26 is a perspective view of the adapter connection portion of FIG. 25 in accordance with an embodiment of the present invention.

Referring to FIG. 24, locking member 170 also provides a physical barrier to prevent plunger rod 44 from compressing stopper 40 and traveling back within cartridge 18 after flexible arms 54 of plunger rod 44 have moved beyond locking member 170 as shown in FIG. 24. With plunger rod 44 in an initial position, flexible arms 54 of plunger rod 44 are deformed by locking member 170 so that plunger rod 44 is capable of actuating stopper 40 from the first position to the second position. After plunger rod 44 actuates stopper 40 from the second position back to the first position and flexible arms 54 of plunger rod 44 are advanced beyond locking member 170 as shown in FIG. 24, flexible arms 54 of plunger rod 44 move to the non-deformed position and lock to locking member 170 as shown in FIG. 24. In this manner, locking member 170 prevents plunger rod 44 from actuating stopper 40 again from the first position to the second position, thereby preventing injection by plunger 44.

Referring to FIGS. 13 and 14, in one embodiment, locking member 170 may also include an elastomeric layer or gasket 178 which is disposed between locking member 170 and cartridge 18 which may be formed of glass to protect and constrain cartridge 18. Gasket 178 may be either overmolded to locking member 170 or inserted in cartridge housing 12 and placed above cartridge 18 so that when locking member 170 is secured to cartridge housing 12, gasket 178 is disposed between cartridge 18 and locking member 170.

Before cartridge housing 12 is removed from adapter assembly 14 (with cartridge housing 12 connected to cartridge housing connection portion 114 of needle adapter 82), and after a first substance or liquid contained within chamber 38 of cartridge 18 has been expelled and mixed with a second substance or powder contained within vial 16 and the mixture of substances transferred back into chamber 38 of cartridge 18 via adapter assembly 14 as discussed above, rotation of cartridge housing 12 while connected to adapter assembly 14 causes locking tabs 116 of needle adapter 82 to engage cartridge housing 12. In this manner, upon removal of cartridge housing 12 from adapter assembly 14, needle adapter 82 is connected to cartridge housing 12 which contains cartridge 18 including the mixture of the substances.

At this point, the user may disengage plunger rod 44 from stopper 40, such as by disengaging the threaded engagement therebetween, i.e., stopper connection portion 52 of plunger rod 44 and plunger connection portion 42 of stopper 40, as shown in FIG. 24.

Subsequently, a user may then load or secure cartridge 18 or cartridge holder 12 with cartridge 18 therein containing the reconstituted drug to an injection apparatus such as injector 20, or an autoinjector for injection into a patient, by connecting the holder 12 or alternatively the needle adapter 82 to a connection portion of injector 20. Needle connection portion 110 of needle adapter 82 may be adapted to be attached to injector 20 while tip 37 of cartridge 18 is not directly engageable with a pen needle for injection. In this manner, a user is prevented from accidently securing cartridge 18 containing a pre-constituted liquid to the injector 20 for use in injection to the body of the user.

The drug vial 16 and adapter assembly 14, which are still connected together, can then be discarded. Advantageously, since one end of needle 88 is still inserted into vial 16 and the other end is enclosed within adapter assembly 14, the device can be disposed of without exposing needle 88. Therefore, there is no danger that the user will be pierced by needle 88 while removing cartridge 18 or otherwise handling the device.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A system comprising:
   a cartridge holder having a cartridge holder distal end, a cartridge holder proximal end, and a sidewall extending therebetween and defining an interior adapted to receive a cartridge defining a cartridge chamber;
   a first substance contained within the cartridge chamber;
   a stopper slidably disposed within the cartridge chamber;
   a latch member engageable with a portion of the cartridge holder and a first portion of a plunger rod, wherein the plunger rod is engageable with a portion of the stopper and adapted to communicate with the latch member, the plunger rod comprising a protrusion, wherein the plunger rod is transitionable from a disengaged position, in which the protrusion of the plunger rod is disengaged from the latch member and the latch member is locked to the cartridge holder, to an engaged position, in which the protrusion is engaged with the latch member and the latch member is unlocked from the cartridge holder and locked to the plunger rod;
   a vial defining a vial chamber;
   a second substance contained within the vial chamber; and
   an adapter having a first end adapted to engage the vial and a second end adapted to engage the cartridge holder after engagement with the vial.

2. The system of claim 1, wherein the plunger rod is transitionable from the disengaged position to the engaged position upon distal movement of the plunger rod.

3. The system of claim 1, wherein the plunger rod further comprises a plunger rod distal end engageable with the portion of the stopper and a plunger rod proximal end, the protrusion extending from the plunger rod adjacent the plunger rod proximal end.

4. The system of claim 1, wherein with the plunger rod in the disengaged position, the latch member is locked to the cartridge holder proximal end.

5. The system of claim 4, wherein the stopper is transitionable between a first position adjacent the cartridge holder proximal end and a second position adjacent the cartridge holder distal end.

6. The system of claim 5, wherein with the stopper in the first position the plunger rod is in the disengaged position.

7. The system of claim 5, wherein with the stopper in the second position the plunger rod is in the engaged position.

8. The system of claim 5, wherein actuation of the stopper from the first position to the second position by the plunger rod expels the first substance from the cartridge chamber to the vial chamber via the adapter.

9. The system of claim 1, wherein a second portion of the plunger rod is sized for movement within an interior of the cartridge from the disengaged position to the engaged position.

10. The system of claim 1, wherein the adapter is adapted to engage with the vial and the cartridge holder prior to establishment of fluid communication with the vial or with the cartridge.

11. The system of claim 1, wherein with the vial engaged with the adapter, the adapter is adapted to engage with the cartridge holder such that the cartridge chamber is in fluid communication with the vial chamber via the adapter.

12. The system of claim 11, wherein the stopper is adapted to expel the first substance from the cartridge chamber to the vial chamber via the adapter.

13. The system of claim 1, wherein the first substance comprises a diluent.

14. The system of claim 1, wherein the second substance comprises a powder.

* * * * *